(12) United States Patent
Saligan

(10) Patent No.: US 8,597,883 B2
(45) Date of Patent: Dec. 3, 2013

(54) BIOMARKERS FOR CANCER-RELATED FATIGUE AND USE THEREOF

(75) Inventor: Leorey N. Saligan, Germantown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/396,465

(22) Filed: Feb. 14, 2012

(65) Prior Publication Data

US 2012/0207708 A1 Aug. 16, 2012

Related U.S. Application Data

(60) Provisional application No. 61/442,605, filed on Feb. 14, 2011.

(51) Int. Cl.
*C12Q 1/68* (2006.01)

(52) U.S. Cl.
USPC ........................................................ 435/6.1

(58) Field of Classification Search
None
See application file for complete search history.

(56) References Cited

U.S. PATENT DOCUMENTS

| | | |
|---|---|---|
| 7,462,595 B2 | 12/2008 | Prange et al. |
| 2005/0152908 A1 | 7/2005 | Liew et al. |
| 2006/0275370 A1 | 12/2006 | Chung et al. |
| 2009/0028784 A1 | 1/2009 | Garcia-Martinez et al. |
| 2009/0104187 A1 | 4/2009 | Kovacevich et al. |

FOREIGN PATENT DOCUMENTS

| | | |
|---|---|---|
| WO | WO 2006/031980 | 3/2006 |
| WO | WO 2008/102002 | 8/2008 |

OTHER PUBLICATIONS

Sanchez-Carbayo et al., Journal of Clinical Oncology, 2006, vol. 24, pp. 778-789.*
Bennett et al., "The Experience of Cancer-Related Fatigue and Chronic Fatigue Syndrome: A Qualitative and Comparative Study," *J Pain Symptom Manage*, 34(2):126-135, 2007.
Collado-Hidalgo et al., "Cytokine gene polymorphisms and fatigue in breast cancer survivors: Early finding," *Brain Behav Immun*, 22(8):1197-1200, 2008.
Gow et al., "A gene signature for post-infectious chronic fatigue syndrome," *BMC Med Genomics* 2:38, 2009.
Kerr et al., "Gene Expression Subtypes in Patients with Chronic Fatigue Syndrome/Myalgic Encephalomyelitis," *J Infect Dis* 197:1171-1184, 2008.
Kim et al., The Inhibitory Effect of Pyrroloquinoline Quinone on the Amyloid Formation and Cytotoxicity of Truncated Alpha-Synuclein, *Molecular Neurodegeneration*, 5:20, 2010.
Lamberto et al., "Structural and Mechanistic Basis Behind the Inhibitory Interaction of PcTS on α-synuclein Amyloid Fibril Formation," *Proc Natl Acad Sci USA*, 106(50):21057-21062, 2009.
Landmark-Høyvik et al., "Alterations of Gene Expression in Blood Cells Associated with Chronic Fatigue in Breast Cancer Survivors," *Pharmacogenomics J*, 9:333-340, 2009.
Levine et al., "An Approach to Studies of Cancer Subsequent to Clusters of Chronic Fatigue Syndrome: Use of Data from the Nevada State Cancer Registry," *Clin Infect Dis*, 18(Suppl 1):549-53, 1994.
Levine et al., "Cancer and a Fatiguing Illness in Northern Nevada—A Casual Hypothesis," *Ann Epidemiol*, 8(4):245-249, 1998.
Mustian et al., "Integrative Nonpharmacologic Behavioral Interventions for the Management of Cancer-Related Fatigue," *The Oncologist* 12(Suppl 1):52-67, 2007.
Ohtsuki et al., "The Blood-Brain Barrier Creatine Transporter is a Major Pathway for Supplying Creatine to the Brain," *J Cereb Blood Flow Metab*, 22:1327-335, 2002.
Saligan et al., "Investigating Molecular-Genetic Correlates of Cancer-Related Fatigue," poster presentation for the Multinational Association of Supportive Care conference, Vancouver, Canada, Jun. 23, 2010.
Whistler et al., "Gene expression correlates of unexplained fatigue," *Pharmacogenomics* 7(3):395-405, 2006.

* cited by examiner

*Primary Examiner* — Anne Gussow
*Assistant Examiner* — Mindy G Brown
(74) *Attorney, Agent, or Firm* — Klarquist Sparkman, LLP

(57) ABSTRACT

Described herein is the identification of genes that are significantly up- or down-regulated in patients suffering from cancer-related fatigue (CRF), providing a means for the diagnosis and treatment of CRF. In particular, provided herein is a method of diagnosing a subject with CRF by detecting expression of at least one gene associated with CRF in a sample obtained from the subject; and comparing expression of the at least one gene to a control. Also described herein is a method of treating a patient with CRF by administering to the subject an agent that alters expression or activity of a gene associated with CRF. Further provided is array that includes a plurality of genes associated with CRF, such as TNFRSF25, SLC6A8, OGT, SNCA, APBA2, CASK, OR2W3, MYL4, IL7R, ARHGEF10 and ITGA6.

17 Claims, 10 Drawing Sheets

BIOMARKERS FOR CANCER-RELATED FATIGUE AND USE THEREOF

CROSS REFERENCE TO RELATED APPLICATION

This application claims the benefit of U.S. Provisional Application No. 61/442,605, filed Feb. 14, 2011, which is herein incorporated by reference in its entirety.

FIELD

This disclosure concerns the identification of genes with altered expression in patients with cancer-related fatigue (CRF) and their use in the diagnosis and treatment of patients with CRF.

BACKGROUND

Cancer-related fatigue (CRF) is a symptom experienced by cancer patients at all stages of disease. CRF is defined as a distressing, persistent, subjective sense of tiredness or exhaustion that is not proportional to recent activity and interferes with usual functioning (Cella et al., *J Clin Oncol* 19:3385-3391, 2001). Symptom clusters, such as pain, anorexia, nausea, and fatigue, are associated with cancer and its treatment, but fatigue is reported as the most distressing individual symptom (Curt et al., *Oncologist* 5:353-360, 2000; Vogelzang et al., *Semin Hematol* 34:4-12, 1997). While therapy for cancer-related pain and emesis is advancing (Cella et al., *Oncology* 12:369-377, 1998), there is currently insufficient characterization of CRF, resulting in poor management of patients suffering from this condition.

CRF is a complex phenomenon and its pathophysiology likely involves impairment in muscle physiology and central nervous system (CNS) function. Cancer treatments (such as radiation therapy) initiate an acute inflammatory response, increasing the production of interleukin (IL)-1 and tumor necrosis factor (TNF)-$\alpha$, thereby stimulating the production of IL-6 (Luster et al., *Hepatology* 19:480-488, 1994), all of which have been associated with alterations in muscle physiology, a contributing factor in fatigue (Natelson and Ponzio, *Clin Diagn Lab Immunol* 9:747-752, 2002; Fong et al., *Am J Physiol Regul Integr Comp Physiol* 256:R659-665, 1989). These inflammatory cytokines (e.g., IL-1, IL-6, TNF-$\alpha$) are thought to circulate to CNS structures (Watkins et al., *Life Sci* 57:1011-1026, 1995), causing fatigue by altering neurotransmission in the CNS through the afferent vagus nerve root (Dantzer et al., *Ann NY Acad Sci* 840:586-590, 1998). For example, IL-1 released from activated macrophages is thought to interact with IL-1 receptors in the preoptic nucleus of the hypothalamus (Dinarello, *N Engl J Med* 317:940-945, 1987). The neurons of the preoptic nucleus that synthesize IL-1 have processes with ramifications to other CNS structures, including the limbic system and the brainstem causing modulation of the neural response leading to significant fatigue (Greenberg et al. *J Pain Symptom Management* 8:196-200, 1993).

The symptoms of CRF alone can lead to disability, typically reflected as impaired performance in occupational and interpersonal roles. Although advances in cancer treatments continue to lead to higher cure and survival rates, cancer survivors continue to suffer from CRF, presenting significant challenges for health care providers.

SUMMARY

There is a large unmet need for a better understanding of the mechanisms that initiate and sustain CRF, and the identification of novel targets for therapeutic intervention. Disclosed herein is the identification of genes that are significantly up- or down-regulated in patients suffering from CRF, providing a means for the diagnosis and treatment of CRF.

Provided herein is a method of diagnosing a subject with CRF. In some embodiments, the method includes detecting expression of at least one gene associated with CRF in a sample obtained from the subject; and comparing expression of the at least one gene to a control. In particular examples, the at least one gene is selected from SNCA, SLC25A37 and BCL2L1. An increase in expression of SNCA, SLC25A37 or BCL2L1, or any combination thereof, relative to the control diagnoses the subject with CRF. In other non-limiting examples, the method further includes detecting expression of one or more additional genes associated with CRF, such as IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and/or ARHGEF10.

Methods of treating a subject with CRF are also provided by the present disclosure. In some embodiments, the method includes administering to the subject an agent that alters expression or activity of a gene associated with CRF. In particular examples, the method includes administering to the subject an agent that decreases expression or activity of SNCA, an agent that decreases expression or activity of SLC25A37 and/or an agent that decreases expression or activity of BCL2L1.

The foregoing and other objects, features, and advantages will become more apparent from the following detailed description, which proceeds with reference to the accompanying figures.

DETAILED DESCRIPTION

I. Abbreviations

Figure 1:
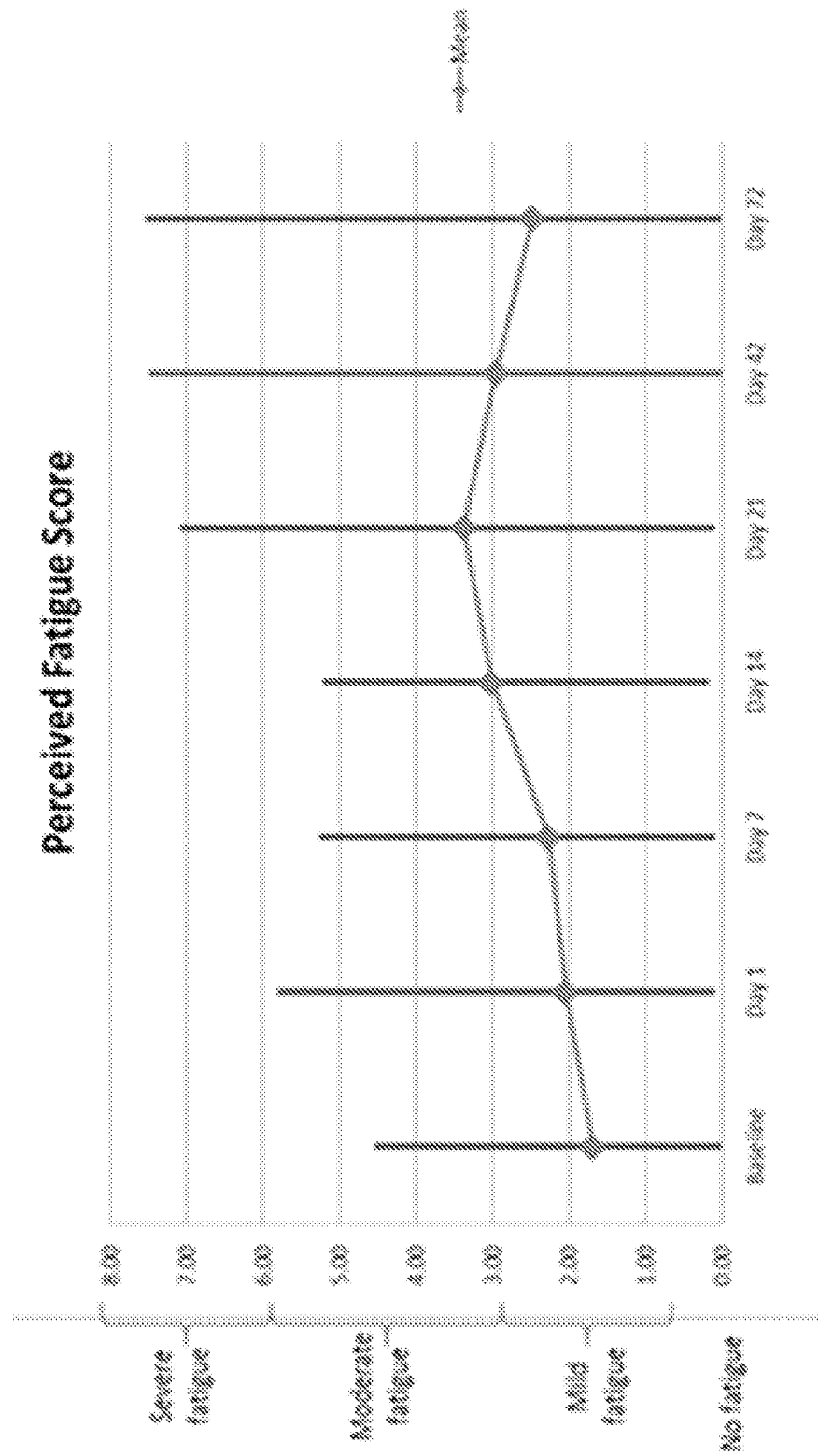
FIG. 1 is a graph showing fatigue scores of study participants with prostate cancer using the revised Piper Fatigue Scale.

AHSP alpha hemoglobin stabilizing protein
APBA2 amyloid beta precursor protein-binding, family A, member 2
ARHGEF10 rho guanine nucleotide exchange factor 10
BCL2L1 BCL2-like 1
BLK B lymphoid tyrosine kinase
CA1 carbonic anhydrase 1
CASK calcium/calmodulin-dependent serine protein kinase
CCR7C—C chemokine receptor type 7
cDNA complementary deoxyribonucleic acid
CNS central nervous system
CRF cancer-related fatigue
cRNA complementary ribonucleic acid
DNA deoxyribonucleic acid
EBRT external beam radiation therapy
ETC electron transport chain
FAIM3 Fas apoptotic inhibitory molecule 3
FCRLA Fc receptor-like A
FDR false detection rate
GYPB glycophorin B
HBD hemoglobin subunit delta
HBG2 hemoglobin subunit gamma-2
IFI27 interferon alpha-inducible protein 27
IGHM Ig mu chain C region
IL interleukin
IL7R interleukin 7 receptor
IMRT intensity modulated radiation therapy
ISCA1 iron-sulfur cluster assembly 1 homolog
ITGA6 integrin, alpha 6
MS4A1 B-lymphocyte antigen CD20
MYL4 myosin, light chain 4, alkali
NSUN5C NOP2/Sun domain family, member 5C
OGT O-linked N-acetylglucosamine (GlcNAc) transferase
OR2W2 olfactory receptor, family 2, subfamilies T2, members 8&3
PAX5 paired box protein Pax-5
POU2AF1 POU domain class 2-associating factor 1
PSA prostate specific antigen
RHCE/RHD blood group Rh(CE) polypeptide
RNA ribonucleic acid
rPFS revised Piper Fatigue Scale
rtPCR real time polymerase chain reaction
SLC6A8 solute carrier family 6 member 8
SLC25A37 solute carrier family 25, member 37
SNCA synuclein alpha
TNF tumor necrosis factor
TNFRSF25 tumor necrosis factor receptor superfamily, member 25
TSH thyroid stimulating hormone
TTC3 tetratricopeptide repeat protein 3
XK X-linked Kx blood group II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent: Any protein, nucleic acid molecule (including chemically modified nucleic acids), compound, small molecule, organic compound, inorganic compound, or other molecule of interest. "Agent" can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, for example ameliorating CRF).

AHSP (Alpha hemoglobin stabilizing protein): A gene encoding an erythroid-specific protein that acts as a molecular chaperone for the free alpha chains of hemoglobin. AHSP is also known as alpha hemoglobin stabilizing protein; erythroid associated factor; erythroid differentiation associated factor; erythroid differentiation-related factor; and erythroid-associated factor. Nucleotide and amino acid sequences for AHSP are publicly available, such as through the NCBI database under Gene ID 51327.

Anemia: A decrease in the number of red blood cells, or less than the normal quantity of hemoglobin in the blood. Treatments for anemia include, for example, iron supplements, vitamin supplements (such as folic acid or vitamin B-12), and blood transfusions.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antisense compound: Refers to an oligomeric compound that is at least partially complementary to the region of a target nucleic acid molecule to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. Target nucleic acid molecules include, for example, mRNAs encoded by CRF-associated genes.

Non-limiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA, miRNA, shRNA or ribozyme.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

APBA2 (amyloid B precursor protein-binding, family A, member 2): A gene that encodes a member of the X11 protein family. The APBA2 protein is a neuronal adapter protein that interacts with the Alzheimer's disease amyloid precursor protein (APP). It stabilizes APP and inhibits production of proteolytic APP fragments including the A beta peptide that is deposited in the brains of Alzheimer's disease patients. This gene product is believed to be involved in signal transduction processes. It is also regarded as a putative vesicular trafficking protein in the brain that can form a complex with the potential to couple synaptic vesicle exocytosis to neuronal cell adhesion. Multiple transcript variants encoding different isoforms have been found for the APBA2 gene. Nucleotide and amino acid sequences for APBA2 are publically available, such as through the NCBI database under Gene ID 321. For example, GenBank Accession Nos. NM_005503 and NP_005494 are nucleotide and amino acid sequences, respectively, of APBA2 isoform a; and GenBank Accession Nos. NM_001130414 and NP_001123886 are nucleotide and amino acid sequences, respectively, of APBA2 isoform b. APBA2 is also known as X11L; MINT2; LIN-10; HsT16821; MGC99508; X11-BETA; D15S1518E; and MGC:14091.

ARHGEF10 (Rho guanine nucleotide exchange factor 10): A gene that encodes a Rho GTPase. Rho GTPases play a fundamental role in numerous cellular processes that are initiated by extracellular stimuli that work through G protein coupled receptors. The ARHGEF10 protein is believed to form complex with G proteins and stimulate Rho-dependent signals. Nucleotide and amino acid sequences for ARHGEF10 are publically available, such as through the NCBI database under Gene ID 9639. For example, GenBank Accession Nos. NM_014629 and NP_055444 are nucleotide and amino acid sequences, respectively, of human ARHGEF10. ARHGEF10 is also known as GEF10; MGC131664; and DKFZp686H0726.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe or antibody) will occur on the array a plurality of times (such as twice), for instance to provide internal controls. The number of addressable locations on the array can vary, for example from at least two, at least three, at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-100 addressable locations, such as 5-50, including 5-15, addressable locations. In particular examples, an array consists essentially of probes or primers or antibodies (such as those that permit amplification or detection) specific for at least one, at least two, at least three, at least four, at least five, at least six, at least seven, at least eight, at least nine, or at least 10 CRF-associated genes disclosed herein, and in some examples, also 1 to 10, such as up to five, control molecules (such as housekeeping genes).

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to at least two, at least three, at least four, at least five, or 10 different CRF-associated molecules, and in some examples also 1 to 10 housekeeping genes.

BLK (B lymphoid tyrosine kinase): A gene encoding a non-receptor tyrosine-kinase of the src family of proto-oncogenes that are typically involved in cell proliferation and differentiation. The protein has a role in B-cell receptor signaling and B-cell development. The BLK protein also stimulates insulin synthesis and secretion in response to glucose and enhances the expression of several pancreatic beta-cell transcription factors. BLK is also known as BLK non-receptor tyrosine kinase; b lymphocyte kinase; p55-Blk; and tyrosine-protein kinase Blk. Nucleotide and amino acid sequences for BLK are publically available, such as through the NCBI database under Gene ID 191305.

CA1 (Carbonic anhydrase 1): A gene belonging to the carbonic anhydrase family. Carbonic anhydrases (CAs) are a large family of zinc metalloenzymes that catalyze the reversible hydration of carbon dioxide. They participate in a variety of biological processes, including respiration, calcification, acid-base balance, bone resorption, and the formation of aqueous humor, cerebrospinal fluid, saliva, and gastric acid. CAs show extensive diversity in tissue distribution and in their subcellular localization. CA1 is closely linked to CA2 and CA3 genes on chromosome 8, and it encodes a cytosolic protein which is found at the highest level in erythrocytes. CA1 is also known as carbonate dehydratase I; carbonic anhydrase 1; carbonic anhydrase B; carbonic dehydratase; CAB; CA-1; and Car1. Nucleotide and amino acid sequences for CA1 are publically available, such as through the NCBI database under Gene ID 759.

Cancer, neoplasia, malignancy, and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, human papilloma virus (HPV)-infected neoplasias, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

In some embodiments, the solid tumor is a prostate cancer, bladder cancer, kidney cancer, pancreatic cancer, melanoma, breast cancer, lung cancer, or colon cancer tumor.

Cancer-related fatigue (CRF): Fatigue that is experienced by nearly all cancer patients, particularly those undergoing chemotherapy, radiation therapy or other types of cancer treatment. The fatigue may be a result of the cancer itself, the cancer treatment, or both. The National Comprehensive Cancer Network defines CRF as a distressing persistent, subjective sense of physical, emotional and/or cognitive tiredness or exhaustion related to cancer or cancer treatment that is not proportional to recent activity and interferes with usual functioning. CRF is a chronic fatigue (persistent fatigue not relieved by rest) but is not related to chronic fatigue syndrome.

CASK (calcium/calmodulin-dependent serine protein kinase): A gene that encodes a calcium/calmodulin-dependent serine protein kinase. The encoded protein is a MAGUK (membrane-associated guanylate kinase) protein family member. These proteins are scaffold proteins and the encoded protein is located at synapses in the brain. Mutations in this gene are associated with FG syndrome 4, mental retardation and microcephaly with pontine and cerebellar hypoplasia, and a form of X-linked mental retardation. Multiple transcript variants encoding different isoforms have been found for this gene. Nucleotide and amino acid sequences for CASK are publically available, such as through the NCBI database under Gene ID 8573. For example, GenBank Accession Nos. NM_003688 and NP_003679 are nucleotide and amino acid sequences, respectively of CASK isoform 1; GenBank Accession Nos. NM_001126054 and NP_001119526 are nucleotide and amino acid sequences, respectively, of CASK isoform 2; and GenBank Accession Nos. NM_001126055 and NP_001119527 are nucleotide and amino acid sequences, respectively, of CASK isoform 3. CASK is also known as CMG; FGS4; LIN2; TNRC8; CAGH39; CAMGUK; MICPCH; FLJ22219; and FLJ31914.

CCR7 (Chemokine (C—C motif) receptor 7): A member of the G protein-coupled receptor family. This receptor was identified as a gene induced by the Epstein-Barr virus (EBV), and is thought to be a mediator of EBV effects on B lymphocytes. CCR7 is expressed in various lymphoid tissues and activates B and T lymphocytes. It has been shown to control the migration of memory T cells to inflamed tissues, as well as stimulate dendritic cell maturation. The chemokine (C—C motif) ligand 19 (CCL19/ECL) has been reported to be a specific ligand of this receptor. CCR7 is also known as C—C CKR-7; C—C chemokine receptor type 7; CC chemokine receptor 7; CC-CKR-7; CCR-7; EBV-induced G protein-coupled receptor 1; EBV-induced G-protein coupled receptor 1; Epstein-Barr virus induced G-protein coupled receptor; Epstein-Barr virus induced gene 1; MIP-3 beta receptor; chemokine (C—C) receptor 7; Epstein-Barr virus-induced G-protein coupled receptor 1; and lymphocyte-specific G protein-coupled peptide receptor. Nucleotide and amino acid sequences for CCR7 are publically available, such as through the NCBI database under Gene ID 1236.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc.; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer.

Consists essentially of: In the context of the arrays of the present disclosure, "consists essentially of" indicates that the expression of additional CRF-associated genes can be evaluated, but not more than ten additional CRF-associated genes. In some examples, "consist essentially of" indicates that no more than 5 other molecules are evaluated, such as no more than 4, 3, 2, or 1 other molecules. In some examples, fewer than the recited molecules are evaluated, but not less than 5, 4, 3, 2 or 1 fewer molecules. In some examples, the expression of one or more controls is evaluated, such as a housekeeping protein or rRNA (such as 18S RNA, beta-microglobulin, GAPDH, and/or 18S rRNA). In this context "consist of" indicates that only the expression of the stated molecules are evaluated; the expression of additional molecules is not evaluated.

Control: A "control" refers to a sample or standard used for comparison with an experimental sample, such as a sample obtained from a subject to be tested for CRF. In some embodiments, the control is a sample obtained from a healthy patient, or a sample obtained from a subject with cancer prior to treatment. In other embodiments, the control is a historical control or reference standard (i.e. a previously tested control sample or group of samples that represent baseline or normal values, such as the level of expression of a CRF-associated gene in a healthy subject).

Detecting expression of a gene: Determining the existence, in either a qualitative or quantitative manner, of a particular nucleic acid or corresponding protein product. Exemplary methods of detecting expression include microarray analysis, RT-PCR, Northern blot, Western blot, immunohistochemistry, ELISA and mass spectrometry.

Diagnosis: The process of identifying a disease by its signs, symptoms and/or results of various tests. The conclusion reached through that process is also called "a diagnosis."

Forms of testing commonly performed include physical exam, blood tests, medical imaging, genetic analysis, urinalysis, and biopsy.

FAIM3 (Fas apoptotic inhibitory molecule 3): This gene encodes an Fc receptor for IgM. Fc receptors specifically bind to the Fc region of immunoglobulins (Igs) to mediate the unique functions of each Ig class. FAIM3 is also known as Fc mu receptor; IgM Fc receptor; fas apoptotic inhibitory molecule 3; immunoglobulin mu Fc receptor; regulator of Fas-induced apoptosis; FCMR; and TOSO. Nucleotide and amino acid sequences for FAIM3 are publically available, such as through the NCBI database under Gene ID 9214.

FCRLA (Fc receptor-like A): This gene encodes a protein similar to receptors for the Fc fragment of gamma immunoglobulin (IgG). These receptors, referred to as FCGRs, mediate the destruction of IgG-coated antigens and of cells induced by antibodies. The FCRLA protein is selectively expressed in B cells, and may be involved in their development. FCRLA may also be involved in the development of lymphomas. FCRLA is also known as Fc receptor homolog expressed in B cells (FREB); Fc receptor related protein X; Fc receptor-like and mucin-like 1; fc receptor homolog expressed in B-cells; fc receptor-like and mucin-like protein 1; fc receptor-like protein; fc receptor-related protein X; FCRL; FCRX; FREB; FCRL1; FCRLX; FCRLb; FCRLd; FCRLe; FCRLM1; FCRLc1; FCRLc2; and RP11-474I16.5. Nucleotide and amino acid sequences for FCRLA are publically available, such as through the NCBI database under Gene ID 84824.

Gene associated with CRF (or CRF-associated gene): Any gene that is up- or down-regulated in a patient with CRF. In some embodiments, CRF-associated genes include any gene listed in Table 2, Table 4 and/or Table 6. In particular embodiments, CRF-associated genes include SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10. In one non-limiting example, the CRF-associated gene is SNCA, SLC25A37 or BCL2L1.

GYPB (Glycophorin B): A major sialoglycoprotein of the human erythrocyte membrane which, along with GYPA, bears the antigenic determinants for the MN and Ss blood groups. GYPB is also known as SS-active sialoglycoprotein; Ss blood group; glycophorin HeP2; glycophorin MiVI; glycophorin-B; sialoglycoprotein delta; SS; GPB; MNS; PAS-3; CD235b; GPB.NY; HGpMiVI; and GYPHe.NY. Nucleotide and amino acid sequences for GYPB are publically available, such as through the NCBI database under Gene ID 2994.

HBD (Hemoglobin delta): A chain of hemoglobin. The delta (HBD) and beta (HBB) genes are normally expressed in the adult: two alpha chains plus two beta chains constitute HbA, which in normal adult life comprises about 97% of the total hemoglobin. Two alpha chains plus two delta chains constitute HbA-2, which with HbF comprises the remaining 3% of adult hemoglobin. Mutations in the HBD gene are associated with beta-thalassemia. HBD is also known as delta globin; delta-globin chain; hemoglobin delta chain; and hemoglobin subunit delta. Nucleotide and amino acid sequences for HBD are publically available, such as through the NCBI database under Gene ID 3045.

HBG2 (Hemoglobin gamma G): A chain of hemoglobin. The gamma globin genes (HBG1 and HBG2) are normally expressed in the fetal liver, spleen and bone marrow. Two gamma chains together with two alpha chains constitute fetal hemoglobin (HbF) which is normally replaced by adult hemoglobin (HbA) at birth. In some beta-thalassemias and related conditions, gamma chain production continues into adulthood. HBG2 is also known as G-gamma globin Paulinia; abnormal hemoglobin; gamma-2-globin; hb F Ggamma; hemoglobin gamma-2 chain; hemoglobin gamma-G chain; hemoglobin subunit gamma-2; methemoglobin; and TNCY. Nucleotide and amino acid sequences for HBG2 are publically available, such as through the NCBI database under Gene ID 3048.

IFI27 (Interferon, alpha-inducible protein 27): A gene encoding an interferon-inducible protein. IFI27 mediates IFN-induced apoptosis characterized by a rapid and robust release of cytochrome C from the mitochondria and activation of BAX and caspases 2, 3, 6, 8 and 9. IFI27 is also known as 2310061N23Rik; ISG12(a); interferon alpha-induced 11.5 kDa protein; interferon alpha-inducible protein 27, mitochondrial; interferon-stimulated gene 12a protein, P27; ISG12; FAM14D; and ISG12A. Nucleotide and amino acid sequences for IFI27 are publically available, such as through the NCBI database under Gene ID 3429.

IGHM (Immunoglobulin heavy constant mu): A gene encoding the C region of the immunoglobulin mu heavy chain, which defines the IgM isotype. Naïve B cells express the transmembrane forms of IgM and IgD on their surface. During an antibody response, activated B cells can switch to the expression of individual downstream heavy chain C region genes by a process of somatic recombination known as isotype switching. In addition, secreted Ig forms that act as antibodies can be produced by alternative RNA processing of the heavy chain C region sequences. Although the membrane forms of all Ig isotypes are monomeric, secreted IgM forms pentamers, and occasionally hexamers, in plasma. IGHM is also known as AGM1, MU, and VH. Nucleotide and amino acid sequences for IGHM are publically available, such as through the NCBI database under Gene ID 3507.

IL7R (interleukin 7 receptor): A gene that encodes a receptor for interleukin 7 (IL7). The function of this receptor requires the interleukin 2 receptor, gamma chain (IL2RG), which is a common gamma chain shared by the receptors of various cytokines, including interleukins 2, 4, 7, 9 and 15. IL7R protein has been shown to play a critical role in V(D)J recombination during lymphocyte development. This protein also controls the accessibility of the TCR gamma locus by STAT5 and histone acetylation. Knockout studies in mice suggested that blocking apoptosis is an essential function of this protein during differentiation and activation of T lymphocytes. The functional defects in IL7R may be associated with the pathogenesis of the severe combined immunodeficiency (SCID). Nucleotide and amino acid sequences for IL7R are publically available, such as through the NCBI database under Gene ID 3573. For example, GenBank Accession Nos. NM_002185 and NP_002176 are nucleotide and amino acid sequences, respectively, of human IL7R. IL7R is also known as ILRA; CD127; IL7RA; CDW127; IL-7R-alpha.

Inhibitor: As used herein, the term "inhibitor" includes any type of molecule that inhibits the expression or activity of a target gene or protein. An inhibitor can be any type of compound, such as a small molecule, antibody or antisense compound.

ISCA1 (Iron-sulfur cluster assembly 1 homolog): A gene encoding a mitochondrial protein involved in the biogenesis and assembly of iron-sulfur clusters, which play a role in electron-transfer reactions. ISCA1 is also known as HESB like domain containing 2; HESB-like domain-containing protein 2; iron sulfur assembly protein IscA; iron-sulfur assembly protein IscA; iron-sulfur cluster assembly 1 homolog, mitochondrial, ISA1; HBLD2; hIscA; and RP11-507D14.2. Nucleotide and amino acid sequences for ISCA1 are publically available, such as through the NCBI database under Gene ID 81689.

ITGA6 (integrin, alpha 6): A gene that encodes integrin alpha chain alpha 6. Integrins are integral cell-surface proteins composed of an alpha chain and a beta chain. A given chain may combine with multiple partners resulting in different integrins. Integrins are known to participate in cell adhesion as well as cell-surface mediated signaling. Two transcript variants encoding different isoforms have been found for this gene. Nucleotide and amino acid sequences for ITGA6 are publically available, such as through the NCBI database under Gene ID 3655. For example, GenBank Accession Nos. NM_001079818 and NP_001073286 are nucleotide and amino acid sequences, respectively, of ITGA6 isoform a; and GenBank Accession Nos. NM_000210 and NP_000201 are nucleotide and amino acid sequences, respectively, of ITGA6 isoform b. ITGA6 is also known as CD49f; VLA-6; ITGA6B; FLJ18737; and DKFZp686J01244.

MicroRNA (miRNA): Single-stranded RNA molecules that regulate gene expression. miRNAs are generally 21-23 nucleotides in length. miRNAs are processed from primary transcripts known as pri-miRNA, to short stem-loop structures called pre-miRNA, and finally to functional miRNA. Mature miRNA molecules are partially complementary to one or more messenger RNA molecules, and their primary function is to down-regulate gene expression. MicroRNAs regulate gene expression through the RNAi pathway.

MS4A1 (Membrane-spanning 4-domains, subfamily A, member 1): A gene encoding a member of the membrane-spanning 4A gene family. Members of this nascent protein family are characterized by common structural features and similar intron/exon splice boundaries and display unique expression patterns among hematopoietic cells and non-lymphoid tissues. MS4A1 encodes a B-lymphocyte surface molecule that plays a role in the development and differentiation of B-cells into plasma cells. MS4A1 is also known as B-lymphocyte antigen CD20; B-lymphocyte cell-surface antigen B1; CD20 antigen; CD20 receptor; leukocyte surface antigen Leu-16, B1; S7; Bp35; CD20; CVID5; MS4A2; and LEU-16. Nucleotide and amino acid sequences for MS4A1 are publically available, such as through the NCBI database under Gene ID 931.

MYL4 (myosin, light chain 4, alkali; atrial, embryonic): A gene encoding a myosin light chain. Myosin is a hexameric ATPase cellular motor protein. It is composed of two myosin heavy chains, two non-phosphorylatable myosin alkali light chains, and two phosphorylatable myosin regulatory light chains. The MYL4 gene encodes a myosin alkali light chain that is found in embryonic muscle and adult atria. Two alternatively spliced transcript variants encoding the same protein have been found for this gene. Nucleotide and amino acid sequences for MYL4 are publically available, such as through the NCBI database under Gene ID 4635. For example, GenBank Accession Nos. NM_001002841 and NP_001002841 are nucleotide and amino acid sequences, respectively, of MYL4 transcript variant 1; and GenBank Accession Nos. NM_002476 and NP_002467 are nucleotide and amino acid sequences, respectively, of MYL4 transcript variant 2. MYL4 is also known as GT1; ALC1; AMLC; and PRO1957.

NSUN5C(NOP2/Sun domain family, member 5 pseudogene 2): This gene shares high sequence similarity with several genes in the Williams Beuren Syndrome critical region and its deletion is associated with this disorder. NSUN5C is also known as NOL1R2, NSUN5C, WBSCR20B, and WBSCR20C. Nucleotide and amino acid sequences for NSUN5C are publically available, such as through the NCBI database under Gene ID 260294.

OGT (O-linked N-acetylglucosamine (GlcNAc) transferase): A gene encoding a glycosyltransferase that catalyzes the addition of a single N-acetylglucosamine in O-glycosidic linkage to serine or threonine residues. Since both phosphorylation and glycosylation compete for similar serine or threonine residues, the two processes may compete for sites, or they may alter the substrate specificity of nearby sites by steric or electrostatic effects. The protein contains multiple tetratricopeptide repeats that are required for optimal recognition of substrates. Alternatively spliced transcript variants encoding distinct isoforms have been found for this gene. Nucleotide and amino acid sequences for OGT are publically available, such as through the NCBI database under Gene ID 8473. For example, GenBank Accession Nos. NM_181672 and NP_858058 are nucleotide and amino acid sequences, respectively, of OGT isoform 1; and GenBank Accession Nos. NM_181673 and NP_858059 are nucleotide and amino acid sequences, respectively, of OGT isoform 2. OGT is also known as HRNT1; FLJ23071; MGC22921; and O-GLCNAC.

Oligonucleotide probe: A short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes. In one example, an oligonucleotide probe is a short sequence of nucleotides used to detect the presence of at least one of the disclosed CRF-associated genes.

OR2W3 (olfactory receptor, family 2, subfamilies T2, members 8&3): A gene encoding an olfactory receptor. Olfactory receptors interact with odorant molecules in the nose, to initiate a neuronal response that triggers the perception of a smell. The olfactory receptor proteins are members of a large family of G-protein-coupled receptors (GPCR) arising from single coding-exon genes. Olfactory receptors share a 7-transmembrane domain structure with many neurotransmitter and hormone receptors and are responsible for the recognition and G protein-mediated transduction of odorant signals. The olfactory receptor gene family is the largest in the genome. Nucleotide and amino acid sequences for OR2W3 are publically available, such as through the NCBI database under Gene ID 343171. For example, GenBank Accession Nos. NM_001001957 and NP_001001957 are nucleotide and amino acid sequences, respectively, of human OR2W3. OR2W3 is also known as OR2W3P; OR2W8P; and OST718.

PAX5 (Paired box 5): This gene encodes a member of the paired box (PAX) family of transcription factors. The central feature of this gene family is a novel, highly conserved DNA-binding motif, known as the paired box. PAX proteins are important regulators in early development, and alterations in the expression of their genes are thought to contribute to neoplastic transformation. This gene encodes the B-cell lineage specific activator protein that is expressed at early, but not late stages of B-cell differentiation. Its expression has also been detected in developing CNS and testis and so the encoded protein may also play a role in neural development and spermatogenesis. PAX5 is also known as B cell specific activator protein; B-cell lineage specific activator; B-cell-specific transcription factor; paired box homeotic gene 5; paired box protein Pax-5; and transcription factor PAX 5.

Nucleotide and amino acid sequences for PAX5 are publically available, such as through the NCBI database under Gene ID 5079.

Pharmaceutical agent or pharmaceutical composition: A compound or composition capable of inducing a desired therapeutic or prophylactic effect when properly administered to a subject or a cell. Pharmaceutical agents can include chemical and/or biological agents.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

POU2AF1 (POU class 2 associating factor 1): A member of a family of transcriptional co-activators that specifically associate with either OCT1 or OCT2 through recognition of their POU domains. The members of this family are essential for the response of B cells to antigens and required for the formation of germinal centers. POU2AF1 is also known as B-cell-specific co-activator OBF-1; BOB-1; OCA-B; OCT-binding factor 1; POU domain class 2-associating factor 1; POU domain, class 2, associating factor 1, BOB1; OBF1; OCAB; and OBF-1. Nucleotide and amino acid sequences for POU2AF1 are publically available, such as through the NCBI database under Gene ID 5450.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Prostate Cancer: A malignant tumor, generally of glandular origin, of the prostate. Prostate cancers include adenocarcinomas and small cell carcinomas. Many prostate cancers express prostate specific antigen (PSA).

Psychostimulant drug: A pharmaceutical agent with antidepressant or mood-elevating properties.

RHCE (Rh blood group, CcEe antigens): A gene encoding the RhC and RhE blood group antigens. The Rh blood group system is the second most clinically significant of the blood groups, second only to ABO. It is also the most polymorphic of the blood groups, with variations due to deletions, gene conversions, and missense mutations. The Rh blood group includes this gene which encodes both the RhC and RhE antigens on a single polypeptide, and a second gene (RHD) which encodes the RhD protein. RHCE is also known as RHCE blood group variant Crawford antigen Rh43; Rh blood group C antigen; Rh blood group Rhce antigen; Rh blood group antigen Evans; Rh polypeptide I; Rhesus blood group CE protein; Rhesus blood group E antigen; Rhesus blood group Rhce antigen; Rhesus system C and E polypeptides; blood group Rh(CE) polypeptide; blood group RhCcEe antigen; rh polypeptide 1; rhesus C/E antigens; rhesus blood group little e antigen; silenced Rh blood group CcEe antigen; RP11-335G20.2; CD240CE; RH; RH30A; RHC; RHE; RHIXB; RHPI; Rh4; RhIVb(J); RhVI; and RhVIII. Nucleotide and amino acid sequences for RHCE are publically available, such as through the NCBI database under Gene ID 6006.

RHD (Rh blood group, D antigen): A gene encoding the RhD blood group antigen. RHD is also known as D antigen (DCS); RH polypeptide 2; Rh blood group antigen Evans; Rhesus system D polypeptide; blood group Rh(D) polypeptide; rhesus D antigen; RP11-335G20.5; CD240D; DIIIc; RH; RH30; RHCED; RHDVA(TT); RHDel; RHPII; RHXIII; Rh4; RhDCw; RhII; RhK562-II; and RhPI. Nucleotide and amino acid sequences for RHD are publically available, such as through the NCBI database under Gene ID 6007.

Ribozyme: A catalytic RNA molecule. In some cases, ribozymes can bind to specific sites on other RNA molecules and catalyze the hydrolysis of phosphodiester bonds in the RNA molecules.

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs.

Sample or biological sample: As used herein, a "sample" obtained from a subject refers to a cell, fluid or tissue sample. Bodily fluids include, but are not limited to, blood, serum, urine and saliva.

SLC6A8 (solute carrier family 6 member 8): A gene encoding a plasma membrane protein whose function is to transport creatine into and out of cells. Defects in this gene can result in X-linked creatine deficiency syndrome. Multiple transcript variants encoding different isoforms have been found for this gene. Nucleotide and amino acid sequences for SLC6A8 are publically available, such as through the NCBI database under Gene ID 6535. For example, GenBank Accession Nos. NM_005629 and NP_005620 are nucleotide and amino acid sequences, respectively, of SLC6A8 isoform 1; GenBank Accession Nos. NM_001142805 and NP_001136277 are nucleotide and amino acid sequences, respectively, of SLC6A8 isoform 2; and GenBank Accession Nos. NM_001142806 and NP_001136278 are nucleotide and amino acid sequences, respectively, of SLC6A8 isoform 3. SLC6A8 is also known as CRT; CT1; CRTR; and MGC87396.

Short hairpin RNA (shRNA): A sequence of RNA that makes a tight hairpin turn and can be used to silence gene expression via the RNAi pathway. The shRNA hairpin structure is cleaved by the cellular machinery into siRNA.

Small interfering RNA (siRNA): A double-stranded nucleic acid molecule that modulates gene expression through the RNAi pathway. siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs."

Small molecule inhibitor: A molecule, typically with a molecular weight less than about 1000 Daltons, or in some embodiments, less than about 500 Daltons, wherein the molecule is capable of inhibiting, to some measurable extent, an activity of a target molecule.

SNCA (synuclein, alpha): A gene encoding alpha-synuclein, a member of the synuclein family, which also includes beta- and gamma-synuclein. Synucleins are abundantly expressed in the brain and alpha- and beta-synuclein inhibit phospholipase D2 selectively. SNCA may serve to integrate presynaptic signaling and membrane trafficking. Defects in SNCA have been implicated in the pathogenesis of Parkinson disease. SNCA peptides are a major component of amyloid plaques in the brains of patients with Alzheimer's disease. Four alternatively spliced transcripts encoding two different isoforms have been identified for this gene. Nucleotide and amino acid sequences for SNCA are publically available, such as through the NCBI database under Gene 6622. For example, GenBank Accession Nos. NM_000345 and NP_000336 are nucleotide and amino acid sequences, respectively, of human SNCA. SNCA is also known as PD1; NACP; PARK1; PARK4; and MGC110988.

Subject: As used herein, the term "subject" includes human and non-human animals. The preferred subject for diagnosis and/or treatment is a human. "Patient" and "subject" are used interchangeably herein.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

Therapeutically effective amount: A quantity of a specific substance sufficient to achieve a desired effect in a subject being treated. For an example not intended to limit the scope of the disclosure, this can be the amount of a pharmaceutical composition comprising an inhibitor of SNCA and/or SLC6A8 to reduce fatigue in a subject with cancer.

TNFRSF25 (tumor necrosis factor receptor superfamily, member 25): A gene encoding a member of the TNF-receptor superfamily. This receptor is expressed preferentially in the tissues enriched in lymphocytes, and it may play a role in regulating lymphocyte homeostasis. TNFRSF25 has been shown to stimulate NF-kappa B activity and regulate cell apoptosis. The signal transduction of this receptor is mediated by various death domain containing adaptor proteins. Knockout studies in mice suggest a role for this gene in the removal of self-reactive T cells in the thymus. Multiple alternatively spliced transcript variants of this gene encoding distinct isoforms have been reported, most of which are potentially secreted molecules. The alternative splicing of this gene in B and T cells encounters a programmed change upon T-cell activation, which predominantly produces full-length, membrane bound isoforms, and is thought to be involved in controlling lymphocyte proliferation induced by T-cell activation. Nucleotide and amino acid sequences for TNFRSF25 are publically available, such as through the NCBI database under Gene ID 8718. For example, GenBank Accession Nos. NM_148965 and NP_683866 are nucleotide and amino acid sequences, respectively, of human TNFRSF25 is also known as DR3; TR3; DDR3; LARD; APO-3; TRAMP; WSL-1; WSL-LR; and TNFRSF12. TNFRSF25 is also known as DR3; TR3; DDR3; LARD; APO-3; TRAMP; WSL-1; WSL-LR; and TNFRSF12.

TTC3 (Tetratricopeptide repeat domain 3): A gene encoding an E3 ubiquitin-protein ligase that mediates the ubiquitination and subsequent degradation of phosphorylated Akt in the nucleus. TTC3 is a terminal regulator of Akt signaling. TTC3 is also known as E3 ubiquitin-protein ligase TTC3; RING finger protein 105; TPR repeat protein 3; TPR repeat protein D; tetratricopeptide repeat protein 3; DCRR1; RNF105; and TPRDIII. Nucleotide and amino acid sequences for TTC3 are publically available, such as through the NCBI database under Gene ID 7267.

XK (X-linked Kx blood group): This locus controls the synthesis of the Kell blood group 'precursor substance' (Kx). Mutations in XK have been associated with McLeod syndrome, an X-linked, recessive disorder characterized by abnormalities in the neuromuscular and hematopoietic systems. The encoded protein has structural characteristics of prokaryotic and eukaryotic membrane transport proteins. XK is also known as Kell blood group precursor (McLeod phenotype); Kx antigen; XK; Kell blood group complex subunit (McLeod syndrome); XK-related protein 1; kell complex 37 kDa component; membrane transport protein XK; KX; MCLDS; X1k; and XKR1. Nucleotide and amino acid sequences for XK are publically available, such as through the NCBI database under Gene ID 7504.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank Accession numbers are incorporated herein by reference as they appear in the NCBI database as of Jan. 25, 2011. In case of conflict, the present specification, including explanations of terms, will control. In addition, the materials, methods, and examples are illustrative only and not intended to be limiting.

III. Overview of Several Embodiments

Disclosed herein are genes that are significantly up- or down-regulated in patients suffering from CRF. The genes identified in the present disclosure serve as biomarkers for the diagnosis and treatment of CRF.

Provided herein is a method of diagnosing a subject with CRF. In some embodiments, the method includes detecting expression of at least one gene associated with CRF in a sample obtained from the subject; and comparing expression of the at least one gene to a control. In particular examples, the at least one gene is selected from SNCA, SLC25A37 and BCL2L1. An increase in expression of SNCA, SLC25A37 or BCL2L1, or any combination thereof, relative to the control diagnoses the subject with CRF. In some instances, expression of SNCA, SLC25A37 or BCL2L1 is increased at least 2-fold, at least 3-fold, at least 4-fold or at least 5-fold relative to the control.

In one non-limiting example, the method includes detecting expression of each of SNCA, SLC25A37 and BCL2L1.

The method of diagnosis may further include detection of one or more additional genes associated with CRF. Thus, in some embodiments, the at least one gene associated with CRF comprises SNCA, SLC25A37 and/or BCL2L1, and further comprises one or more genes selected from IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10. An increase in expression of SNCA, SLC25A37, BCL2L1, IFI27, CA1, HBD, XK, HBG2, RHCE/RHD, AHSP, GYPB, ISCA1, SLC6A8, OR2W3 and/or MYL4, or a decrease in expression of MS4A1, IGHM, PAX5, FCRLA, TTC3, NSUN5C, POU2AF1, CCR7, FAIM3, BLK, TNFRSF25, OGT, APBA2, CASK, IL7R, ITGA6 and/or ARHGEF10, or any combination thereof, diagnoses the patient with CRF.

Detecting expression of the at least one gene associated with CRF can be accomplished using any suitable method known in the art (such as one of the methods described in section IV below). In some embodiments, detecting expression of the at least one gene comprises detecting mRNA expression of the at least one gene. In some examples, RT-PCR or microarray analysis is performed to detect mRNA expression of a CRF-associated gene. In other embodiments, detecting expression of the at least one gene comprises detecting protein encoded by the at least one gene, such as by ELISA or immunoblot.

In one non-limiting example, such as when detecting expression of multiple CRA-associated genes is desirable, detecting expression of the at least one gene comprises microarray analysis using a solid support with probes specific for the at least one gene.

The control used in the disclosed methods can be any suitable control that provides a normal or baseline value for expression of a CRF-associated gene. In some embodiments, the subject has undergone or is currently undergoing treatment for cancer and the control is a sample obtained from the subject prior to the treatment. In other embodiments, the control is a reference value or a set of reference values. In yet other embodiments, the control is a sample obtained from a healthy subject.

In some embodiments, the sample is a bodily fluid sample, such as a blood sample. In other embodiments, the sample is a tissue sample, such as a tumor biopsy.

The methods of diagnosing CRF are contemplated for subjects with any type of cancer, including solid tumors and hematologic cancers. In some embodiments, the solid tumor is prostate cancer, lung cancer, breast cancer, colon cancer, bladder cancer, kidney cancer, melanoma, pancreatic cancer or thyroid cancer. In some embodiments, the hematologic cancer is a leukemia or lymphoma.

In addition, the methods of diagnosis disclosed herein are contemplated for use in cancer subjects that are currently undergoing treatment, have previously undergone treatment or have not yet been treated for cancer.

In some embodiments, the subject has undergone or is currently undergoing treatment for cancer. The treatment can include, for example, radiation therapy, chemotherapy, targeted therapy, immunotherapy, hormonal therapy, angiogenesis inhibitor therapy, surgery, or any combination thereof. Cancer treatments are well known in the art and are discussed further in section VI below.

In one non-limiting example, the subject has prostate cancer and has undergone or is currently undergoing treatment with radiation therapy.

In some embodiments of the methods of diagnosis, the method further includes selecting an appropriate therapy for the subject and/or administering an appropriate therapy for the subject. For example, an appropriate therapy for the subject may be an inhibitor of a CRF-associated gene (such as SNCA, SLC25A37 or BCL2L1) that is up-regulated in the subject. In some embodiments, the appropriate therapy includes a psychostimulant drug, a treatment for anemia, cognitive behavior therapy, exercise, or any combination thereof.

Also provided herein is a method of treating a patient with CRF. In some embodiments, the method includes administering to the subject an agent that alters expression or activity of a gene associated with CRF. In particular examples, the method includes administering an agent decreases expression or activity of SNCA, administering an agent that decreases expression or activity of SLC25A37 or an agent that decreases expression or activity of BCL2L1. The method may further include administering one or more additional therapies, such as a psychostimulant drug, a treatment for anemia (such as a blood transfusion), cognitive behavior therapy, exercise, or any combination thereof.

The agent can be any type of compound that alters expression or activity of a CRF-associated gene. For example, the agent can be a small molecule, antibody or antisense compound. Antisense compounds include, for example, antisense oligonucleotides, siRNAs, miRNAs, shRNAs and ribozymes.

In some embodiments, the subject is administered an agent that decreases expression or activity of SNCA, SLC25A37 or BCL2L1 and is further administered a second agent. The second agent increases expression or activity of MS4A1, IGHM, PAX5, FCRLA, TTC3, NSUN5C, POU2AF1, CCR7, FAIM3, BLK, TNFRSF25, OGT, APBA2, CASK, IL7R, ITGA6 or ARHGEF10, or any combination thereof; or decreases expression or activity of IFI27, CA1, HBD, XK, HBG2, RHCE/RHD, AHSP, GYPB, ISCA1, SLC6A8, OR2W3 or MYL4, or any combination thereof.

In some cases, the subject to be treated has already undergone, is currently undergoing or will later undergo another treatment for cancer, such as chemotherapy, radiation therapy, targeted therapy, immunotherapy, hormonal therapy, angiogenesis inhibitor therapy, surgery or any combination thereof.

Methods of monitoring a treatment for CRF are also provided herein. In some embodiments, the method includes detecting expression of at least one gene associated with CRF in a sample obtained from the subject that is undergoing or that has recently undergone treatment; and comparing expression of the at least one gene to a control, such as a sample obtained from the subject prior to treatment. In particular examples, the at least one gene is selected from SNCA, SLC25A37 and BCL2L1. A decrease in expression of SNCA, SLC25A37 and/or BCL2L1, relative to the control indicates the treatment is effective in treating CRF.

Further provided herein is array that includes a plurality of genes associated with CRF. In some embodiments, the array consists essentially of a plurality of CRF-associated genes. In particular examples, the array consists essentially of probes specific for at least 2, at least 3, at least 4, at least 5, at least 6, at least 7, at least 8, at least 9, or at least 10 CRF-associated genes selected from the group consisting of SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10, and up to five housekeeping genes.

IV. Detecting Expression of CRF-Associated Genes

As described below, expression of one or more CRF-associated genes can be detected using any one of a number of methods well known in the art. Expression of either mRNA or protein is contemplated herein.

A. Methods for Detection of CRF-associated mRNA Gene expression can be evaluated by detecting mRNA of the gene of interest. Thus, the disclosed methods can include evaluating mRNA of any CRF-associated gene (e.g. SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 or ARHGEF10). In some examples, the mRNA is quantified.

RNA can be isolated from a sample using methods well known to one skilled in the art, including commercially available kits. The sample can be obtained from a subject with cancer and/or a control subject. The sample can be any suitable biological sample, such as a bodily fluid sample (such as blood) or a tissue sample (such as a tumor tissue sample). In some embodiments, the sample is a blood sample.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker (Lab Invest. 56:A67, 1987), and De Andres et al. (*BioTechniques* 18:42044, 1995). An exemplary method of mRNA isolation from blood samples is provided in Example 1 below. In another example, RNA isolation can be performed using a purification kit, buffer set and protease from commercial manufacturers, such as QIAGEN™, according to the manufacturer's instructions. For example, total RNA from cells in a sample (such as those obtained from a subject) can be isolated using QIAGIN™ RNeasy mini-columns. Other commercially available RNA isolation kits include MASTERPURE™. Complete DNA and RNA Purification Kit (EPICENTRE™ Madison, Wis.), and Paraffin Block RNA Isolation Kit (Ambion, Inc.). Total RNA from tissue samples can be isolated using RNA Stat-60 (Tel-Test). RNA prepared from a biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using northern blotting or in situ hybridization (Parker & Barnes, Methods in Molecular Biology 106:247-283, 1999); RNAse protection assays (Hod, *Biotechniques* 13:852-854, 1992); and PCR-based methods, such as reverse transcription polymerase chain reaction (RT-PCR) (Weis et al., *Trends in Genetics* 8:263-264, 1992). Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples (such as samples from cancer subjects and healthy subject, or before or after therapy) to characterize patterns of gene expression.

Methods for quantifying mRNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp™ RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan™ PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN™ RT-PCR can be performed using commercially available equipment, such as, for example, ABI PRISM 7700™ Sequence Detection System™ (Perkin-Elmer-Applied Biosystems, Foster City, Calif.), or Lightcycler (Roche Molecular Biochemicals, Mannheim, Germany). In one example, the 5' nuclease procedure is run on a real-time quantitative PCR device such as the ABI PRISM 7700™ Sequence Detection System™. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g., TAQMAN™ probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., *Genome Research* 6:986-994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available, for example, from PE Applied Biosystems, under the trademark ABI PRISM™ 7700.

The steps of a representative protocol for quantifying gene expression using fixed, paraffin-embedded tissues as the RNA source, including mRNA isolation, purification, primer extension and amplification are given in various publications (see Godfrey et al., *J. Mol. Diag.* 2:84-91, 2000; Specht et al., *Am. J. Pathol.* 158:419-429, 2001). Briefly, a representative process starts with cutting about 10 μm thick sections of paraffin-embedded tumor tissue samples or adjacent non-cancerous tissue. The RNA is then extracted, and protein and DNA are removed. Alternatively, RNA is located directly from a tumor sample or other tissue sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 or ARHGEF10 mRNA (or any gene disclosed herein as either up-regulated or down-regulated in CFR patients relative to a control). In some embodiments, expression of other genes is also detected. Primers that can be used to amplify SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 or ARHGEF10 (or any other gene of interest) are commercially available or can be designed and synthesized according to well known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "housekeeping" gene or "internal control" can also be evaluated. These terms include any constitutively or globally expressed gene whose presence enables an assessment of CRF-associated gene mRNA levels. Such an assessment includes a determination of the overall constitutive level of gene transcription and a control for variations in RNA recovery.

In some examples, gene expression is identified or confirmed using the microarray technique. In this method, CRF-associated gene nucleic acid sequences of interest (including cDNAs and oligonucleotides) are plated, or arrayed, on a microchip substrate. The arrayed sequences are then hybridized with specific DNA probes from cells or tissues of interest.

In a specific embodiment of the microarray technique, PCR amplified inserts of cDNA clones are applied to a substrate in a dense array. At least probes specific for two or more of CRF-associated gene nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously.

The miniaturized scale of the hybridization affords a convenient and rapid evaluation of the expression pattern for CRF-associated genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):10614-10619, 1996). Microarray analysis can be performed by commercially available equipment, following manufacturer's protocols, such as are supplied with Affymetrix GeneChip™ technology, or Incyte's microarray technology.

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of CRF-associated genes.

Sample cells or tissues are treated to increase their permeability to allow a probe, such as a CRF-associated gene-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a blood sample obtained from a subject with CRF. Since the sequences of the CRF-associated genes of interest are known, probes can be designed accordingly such that the probes specifically bind the gene of interest.

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

B. Arrays for Profiling CRF-associated Gene Expression

In particular embodiments provided herein, arrays are provided that can be used to evaluate CRF-associated gene expression, for example to diagnose a patient with CRF. When describing an array that consists essentially of probes or primers specific for a set or subset of CRF-associated genes, such an array includes probes or primers specific for the specific set or subset of CRF-associated genes, and can further include control probes (for example to confirm the incubation conditions are sufficient). In some examples, the array may further comprise additional, such as 1, 2, 3, 4 or 5 additional CRF-associated genes. In other examples, the array may include fewer, such as 1, 2, 3, 4 or 5 fewer CRF-associated genes. Exemplary control probes include GAPDH, actin, and YWHAZ. In one example, an array is a multi-well plate (e.g., 98 or 364 well plate).

In one example, the array includes, consists essentially of, or consists of probes or primers (such as an oligonucleotide or antibody) that can recognize at least 2, at least 3, at least 4, at least 5, at least 6, at least 7, at least 8, at least 9, or at least 10 CRF-associated genes selected from the group consisting of SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10, and up to five housekeeping genes. The oligonucleotide probes or primers can further include one or more detectable labels, to permit detection of hybridization signals between the probe and target sequence (such as one of the CRF-associated genes disclosed herein).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554, 501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second(2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

C. Methods for Detection of Protein Encoded by a CRF-Associated Gene

In some examples, expression of a protein encoded by a CRF-associated gene is analyzed. Antibodies specific for CRF-associated proteins can be used for detection and quantification of the proteins by one of a number of immunoassay methods that are well known in the art, such as those presented in Harlow and Lane (*Antibodies, A Laboratory Manual*, CSHL, New York, 1988). Methods of constructing such antibodies are known in the art.

Any standard immunoassay format (such as ELISA, Western blot, or RIA assay) can be used to measure protein levels. Thus, CRF-associated polypeptide levels in a sample (such as a blood sample) can readily be evaluated using these methods. Immunohistochemical techniques can also be utilized for CRF-associated protein detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying CRF-associated proteins, a biological sample of the subject that includes cellular proteins can be used. Quantification of protein can be achieved by immunoassay methods known in the art. The amount protein can be assessed in samples from cancer patients and/or in samples from cancer-free subjects. The amounts of CRF-associated protein in the sample can be compared to a control, such as the levels of the proteins found in cells from a cancer-free subject or other control (such as a standard value or reference value). A significant increase or decrease in the amount can be evaluated using statistical methods disclosed herein and/or known in the art.

Quantitative spectroscopic approaches methods, such as SELDI, can be used to analyze CRF-associated protein expression in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example, see U.S. Pat. Nos. 5,719,060; 6,897,072; and 6,881, 586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as CRF-associated proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as CRF-associated proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind at least 2, at least 3, at least 4, at least 5, at least 6, at least 7, at least 8, at least 9, or at least 10 CRF-associated proteins selected from the group consisting of SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10. In other examples, the chromatographic surface consists essentially of, or consists of, antibodies that specifically bind SNCA, SLC25A37, BCL2L1, IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10. In some examples, the chromatographic surface includes antibodies that bind other molecules, such as housekeeping proteins (e.g. actin or myosin).

In another example, antibodies are immobilized onto the surface using a bacterial Fc binding support. The chromatographic surface is incubated with a sample, such as a blood sample. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

V. Agents for the Treatment of CRF

The methods for treating CRF contemplate the use of any compound that modulates expression or activity of a CRF-associated gene (a gene that is up- or down-regulated in patients with CRF), such as any one of the genes listed in Table 2, Table 4 and/or Table 6. Agents for the treatment of CRF can include, for example, small molecules, antisense compounds or antibodies.

A. Small Molecules

Any small molecule that inhibits expression or activity of a CRF-associated gene is contemplated for use in the disclosed methods. Methods of identifying small molecule inhibitors to a specific molecule are within the abilities of one of skill in the art. Moreover, small molecule inhibitors of at least some of the CRF-associated have genes have been previously described.

Small molecule inhibitors of SNCA have been previously described. For example, Masuda et al. (*Biochemistry* 45(19): 6085-6094, 2006) disclose numerous small molecule inhibitors of alpha-synuclein filament assembly; Kim et al. (*Mol Neurodegener* 5:20, 2010) teach that pyrroloquinoline quinone (PQQ) inhibits fibril formation of alpha-synuclein; and Lamberto et al. (*Proc Natl Acad Sci USA* 106(50):21057-21062, 2009) describe the inhibitory effect of phthalocyanine tetrasulfonate (PcTS) on alpha-synuclein amyloid fibril formation.

SLC6A8 inhibitors are also known in the art, including β-guanidinopropionate and guanidinoacetate (Ohtsuki et al., *J Cereb Blood Flow Metab* 22:1327-1335, 2002).

Methods of screening for compounds that inhibit expression or activity of a particular gene (or gene product) are well known in the art and any suitable assay can be used to identify inhibitors of a CRF-associated gene.

B. Antisense Compounds

Generally, the principle behind antisense technology is that an antisense compound hybridizes to a target nucleic acid and effects the modulation of gene expression activity, or function, such as transcription, translation or splicing. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide. Antisense oligonucleotides can also be used to modulate gene expression, such as splicing, by occupancy-based inhibition, such as by blocking access to splice sites.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Another type of antisense compound that utilizes the RNAi pathway is microRNA. MicroRNAs are naturally occurring RNAs involved in the regulation of gene expression. However, these compounds can be synthesized to regulate gene expression via the RNAi pathway. Similarly, shRNAs are RNA molecules that form a tight hairpin turn and can be used to silence gene expression via the RNAi pathway. The shRNA hairpin structure is cleaved by the cellular machinery into siRNA.

Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a messenger RNA.

Each of the above-described antisense compounds provides sequence-specific target gene regulation. This sequence-specificity makes antisense compounds effective tools for the selective modulation of a target nucleic acid of interest.

In some embodiments, expression of the CRF-associated gene is inhibited at least about 10%, at least about 25%, at least 50%, at least 75%, at least 90%, or at least 95% relative to a control. Any type of antisense compound that specifically targets and regulates expression of a CRF-associated gene is contemplated for use with the disclosed methods. Such antisense compounds include single-stranded compounds, such as antisense oligonucleotides, and double-stranded compounds, including compounds with at least partial double-stranded structure, including siRNAs, miRNAs, shRNAs and ribozymes. Methods of designing, preparing and using antisense compounds that specifically target a nucleic acid molecule encoding a CRF-associated gene are within the abilities of one of skill in the art. Furthermore, sequences for CRF-associated genes are publicly available (see Terms and Methods for exemplary GenBank Accession Numbers, which are herein incorporated by reference as they appear in the GenBank database as of Jan. 25, 2011). The specific GenBank Accession numbers listed herein are provided for reference only and are not intended to be limiting.

Antisense compounds specifically targeting a CRF-associated gene nucleic acid molecule can be prepared by designing compounds that are complementary to the CRF-associated gene nucleotide sequence, particularly the CRF-associated gene mRNA sequence. Antisense compounds targeting a CRF-associated gene need not be 100% complementary to the CRF-associated gene to specifically hybridize and regulate expression the target gene. For example, the antisense compound, or antisense strand of the compound If a double-stranded compound, can be at least 75%, at least 80%, at least 85%, at least 90%, at least 95%, at least 99% or 100% complementary to the selected CRF-associated gene nucleic acid sequence. Methods of screening antisense compounds for specificity are well known in the art (see, for example, U.S. Patent Application Publication No. 2003/0228689).

Antisense compounds specific for at least some of the CRF-associated genes disclosed herein have been previously described. For example, siRNA inhibitors specific for SNCA are disclosed in U.S. Patent Application Publication Nos. 2008/0139799; 2004/0219671; 2005/0186591; 2007/0161595; 2009/0176729; and 2005/0137155.

In some examples, the antisense compounds described herein contain one or more modifications to enhance nuclease resistance and/or increase activity of the compound. Modified antisense compounds include those comprising modified backbones or non-natural internucleoside linkages. As defined herein, antisense compounds having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (*Science* 254, 1497-1500, 1991).

Modified antisense compounds can also contain one or more substituted sugar moieties. In some examples, the antisense compounds can comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv Chim Acta* 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Antisense compounds can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993). Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066;

5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692.

C. Antibodies

Antibodies contemplated for use in the methods provided herein include, for example, monoclonal and polyclonal antibodies specific for a protein, or fragment thereof, encoded by a CRF-associated gene.

Methods of making polyclonal and monoclonal antibodies are well known, and are described below. Polyclonal antibodies, antibodies which consist essentially of pooled monoclonal antibodies with different epitopic specificities, as well as distinct monoclonal antibody preparations are included. The preparation of polyclonal antibodies is well known to those skilled in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992).

The preparation of monoclonal antibodies likewise is conventional (see, for example, Kohler & Milstein, *Nature* 256: 495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465; and Losman et al., *Int J Cancer* 46:310, 1990.

Alternatively, an antibody that specifically binds a protein encoded by a CRF-associated gene can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc Natl Acad Sci USA* 89:4285, 1992; Sandhu, Crit. Rev Biotech 12:437, 1992; and Singer et al., *J Immunol* 150:2844, 1993.

Antibodies can be derived from human antibody fragments isolated from a combinatorial immunoglobulin library (see, for example, Barbas et al., in: *Methods: a Companion to Methods in Enzymology*, Vol. 2, page 119, 1991; Winter et al., *Ann. Rev. Immunol.* 12:433, 1994). Cloning and expression vectors that are useful for producing a human immunoglobulin phage library can be obtained, for example, from Stratagene Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int Immunol* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody, defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch Biochem Biophys* 89:230, 1960; Porter, *Biochem J* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc Natl Acad Sci USA* 69:2659, 1972). Alternatively, the variable chains can be linked by an intermolecular disulfide bond or cross-linked by chemicals such as glutaraldehyde (see, for example, Sandhu, *Crit. Rev Biotech* 12:437, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, *Crit. Rev Biotech* 12:437, 1992).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin, thyroglobulin, bovine serum albumin, and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

Binding affinity for a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D$=1/K, where K is the affinity constant) of the antibody is, for example <1 µM, <100 nM, or <0.1 nM. Antibody molecules will typically have a $K_D$ in the lower ranges. $K_D$=[Ab-Ag]/[Ab] [Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

D. Administration of Therapeutic Agents

Therapeutic agents for the treatment of CRF can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. A therapeutic agent can be administered using any suitable route, including, for example, parenteral, oral or topical.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Administration can be accomplished by single or multiple doses. The dose required will vary from subject to subject depending on the species, age, weight and general condition of the subject, the particular type of therapeutic agent being used and its mode of administration. An appropriate dose can be determined by one of ordinary skill in the art using only routine experimentation. If administered in multiple doses, the time between delivery of each dose can vary between days, weeks, months and years.

Therapeutic agents for the treatment of CRF can be administered in combination with one or more cancer therapies, such as chemotherapy, radiation therapy, immunotherapy, hormonal therapy, angiogenesis inhibitor therapy, surgery, or any other known treatment for cancer, or combination thereof. Additional cancer treatments are known in the art, some of which are discussed below.

VI. Cancer Treatments

In some embodiments of the methods discussed herein, the subject may receive (or have received) one or more standard treatments for cancer. Such treatment can further be administered in combination with one or more agents that modulate expression or activity of a CRF-associated gene.

Exemplary treatments for cancer include, but are not limited to, chemotherapy, radiation therapy, immunotherapy, hormonal therapy, angiogenesis inhibitor therapy, and surgery.

A. Chemotherapy

Chemotherapy is the treatment of cancer with drugs that can destroy cancer cells. The term "chemotherapy" generally refers to cytotoxic drugs which affect rapidly dividing cells in general. Chemotherapy drugs interfere with cell division in various possible ways, e.g. with the duplication of DNA or the separation of newly formed chromosomes. Most forms of chemotherapy target all rapidly dividing cells and are not specific to cancer cells, although some degree of specificity may come from the inability of many cancer cells to repair DNA damage, while normal cells generally can. Hence, chemotherapy has the potential to harm healthy tissue, especially those tissues that have a high replacement rate (e.g. intestinal lining). These cells usually repair themselves after chemotherapy.

Examples of some of the most commonly used chemotherapy drugs include adriamycin, alkeran, Ara-C, BiCNU, busulfan, CCNU, carboplatinum, cisplatinum, cytoxan, daunorubicin, DTIC, 5-FU, fludarabine, hydrea, idarubicin, ifosfamide, methotrexate, mithramycin, mitomycin, mitoxantrone, nitrogen mustard, taxol (or other taxanes, such as docetaxel), velban, vincristine, VP-16, while some more newer drugs include gemcitabine (Gemzar™), Herceptin™, irinotecan (Camptosar™, CPT-11), leustatin, navelbine, Rituxan™, STI-571, Taxotere™, topotecan (Hycamtin™), Xeloda™ (capecitabine), zevelin and calcitriol.

Chemotherapeutic agents include, for example, alkylating agents, antimetabolites, natural products, topoisomerase inhibitors, antineoplastic agents, other miscellaneous agents, or any combination of these. As will be understood to one of skill in the art, some chemotherapeutic agents fall within more than one of the above-listed categories.

Examples of alkylating agents include, but are not limited to, nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine), ciplastin, carboplatin, oxaliplatin, and ifosfamide.

Examples of antimetabolites include, but are not limited to, folic acid analogs (such as methotrexate), pyrimidine analogs (such as 5-FU or cytarabine), and purine analogs, such as mercaptopurine, thioguanine or azathioprine.

Examples of natural products include, but are not limited to, vinca alkaloids (such as vinblastine, vincristine, vinorelbine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Examples of miscellaneous chemotherapeutic agents include, but are not limited to, platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Examples of topoisomerase inhibitors include, but are not limited to, type I topoisomerase inhibitors, such as camptothecins (e.g. irinotecan and topotecan) and type II topoisomerase inhibitors, such as amsacrine, etoposide, etoposide phosphate, and teniposide (which are semisynthetic derivatives of epipodophyllotoxins).

Antineoplastics include, for example, the immunosuppressant dactinomycin, doxorubicin, epirubicin and bleomycin.

B. Radiation Therapy

Radiation therapy is also referred to as radiotherapy, X-ray therapy or irradiation. Radiation therapy involves the use of ionization radiation to kill cancer cells and shrink tumors. Radiation therapy can be administered externally via external beam radiotherapy (EBRT) or internally via brachytherapy. The effects of radiation therapy are localized and confined to the region being treated. Radiation therapy injures or destroys cells in the area being treated (the "target tissue") by damaging their genetic material, making it impossible for these cells to continue to grow and divide. Although radiation damages both cancer cells and normal cells, most normal cells can recover from the effects of radiation and function properly. The goal of radiation therapy is to damage as many cancer cells as possible, while limiting harm to nearby healthy tissue.

Radiation therapy may be used to treat almost every type of solid tumor, including cancers of the brain, breast, cervix, larynx, lung, pancreas, prostate, skin, stomach, uterus, or soft tissue sarcomas. Radiation is also used to treat leukemia and lymphoma. Radiation dose to each site depends on a number of factors, including the radiosensitivity of each cancer type and whether there are tissues and organs nearby that may be damaged by radiation.

C. Immunotherapy

Cancer immunotherapy refers to a diverse set of therapeutic strategies designed to induce the patient's own immune system to fight the tumor. Contemporary methods for generating an immune response against tumors include intravesical BCG immunotherapy for superficial bladder cancer, and use of interferons and other cytokines to induce an immune response in renal cell carcinoma and melanoma patients. Vaccines to generate specific immune responses are the subject of intensive research for a number of tumors, notably malignant melanoma and renal cell carcinoma. Sipuleucel-T is a vaccine-like strategy in late clinical trials for prostate cancer in which dendritic cells from the patient are loaded with prostatic acid phosphatase peptides to induce a specific immune response against prostate-derived cells.

Allogeneic hematopoietic stem cell transplantation (bone marrow transplantation from a genetically non-identical donor) is also considered a form of immunotherapy since the donor's immune cells will often attack the tumor in a phenomenon known as graft-versus-tumor effect. For this reason, allogeneic HSCT leads to a higher cure rate than autologous transplantation for several cancer types.

Immunotherapy includes administration of monoclonal antibodies that specifically recognize tumor antigens. Exemplary monoclonal antibodies for the treatment of cancer include alemtuzumab (targeting CD52) bevacizumab (targeting VEGF); cetuximab (targeting EGFR), gemtuzumab ozogamicin (targeting CD33), ibritumomab tiuxetan (targeting CD20), panitumumab (targeting EGFR), rituximab (targeting CD20), and trastuzumab (targeting ErbB2).

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

D. Hormonal Therapy

The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens (e.g., progesterone) may be therapeutically beneficial.

Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

E. Angiogenesis Inhibitor Therapy

Angiogenesis inhibitors prevent the extensive growth of blood vessels (angiogenesis) that tumors require to survive. Some, such as bevacizumab, have been approved and are in clinical use.

Examples of angiogenesis inhibitors include, but are not limited to bevacizumab, carboxyamidotriazole, TNP-470, CM101, IFN-α, IL-12, platelet factor-4, suramin, SU5416, VEGFR antagonists, angiostatic steroids in combination with heparin, cartilage-derived angiogenesis inhibitory factor, matrix metalloproteinase inhibitors, angiostatin, endostatin, 2-methoxyestradiol, tecogalan, tetrathiomolybdate, thalidomide, thrombospondin, prolactin, $\alpha_v\beta_3$ inhibitors and linomide.

F. Targeted Therapy

Targeted therapy is a type of medication that blocks the growth of cancer cells by interfering with specific targeted molecules needed for carcinogenesis and tumor growth, rather than by simply interfering with rapidly dividing cells (e.g. with traditional chemotherapy). Targeted cancer therapies may be more effective than current treatments and less harmful to normal cells. The two primary categories of targeted therapy are small molecules and monoclonal antibodies.

Non-limiting examples of small molecules include imatinib mesylate (also known as Gleevec™), gefitinib (also known as Iressa™ or ZD1839), erlotinib (Tarceva™), bortezomib (Velcade™), tamoxifen, BCL-2 antagonists (such as obatoclax, ABT-263 and gossypol), PARP inhibitors (such as iniparib and olaparib), Janus kinase inhibitors, apatinib and salinomycin.

Non-limiting examples of monoclonal antibodies include rituximab, trastuzumab, cetuximab and bevacizumab.

G. Surgery

In some instances, non-hematological cancers can be cured if the cancerous tissue is completely removed by surgery. When the cancer has metastasized to other sites in the body prior to surgery, complete surgical excision is usually impossible. In the Halstedian model of cancer progression, tumors grow locally, then spread to the lymph nodes, then to the rest of the body. This has given rise to the popularity of local-only treatments such as surgery for small cancers. Even small localized tumors are increasingly recognized as possessing metastatic potential.

Examples of surgical procedures for cancer include mastectomy for breast cancer, prostatectomy for prostate cancer, and lung cancer surgery for non-small cell lung cancer. The goal of the surgery can be either the removal of only the tumor, or the entire organ. A single cancer cell is invisible to the naked eye but can regrow into a new tumor, a process called recurrence. For this reason, the pathologist will examine the surgical specimen to determine if a margin of healthy tissue is present, thus decreasing the chance that microscopic cancer cells are left in the patient.

In addition to removal of the primary tumor, surgery is often necessary for staging, e.g. determining the extent of the disease and whether it has metastasized to regional lymph nodes. Staging is a major determinant of prognosis and of the need for adjuvant therapy. Occasionally, surgery is necessary to control symptoms, such as spinal cord compression or bowel obstruction. This is referred to as palliative treatment. If surgery is possible and appropriate, it is commonly performed before other forms of treatment. In some instances, surgery must be delayed until other treatments are able to shrink the tumor.

The following examples are provided to illustrate certain particular features and/or embodiments. These examples should not be construed to limit the disclosure to the particular features or embodiments described.

EXAMPLES

Example 1

Materials and Methods

This example describes the experimental procedures used in the studies described in Example 2.

The initial step for evaluating genome-wide changes in peripheral blood of prostate cancer patients receiving EBRT is to explore gene expression changes with microarray technology. It was previously demonstrated that the Affymetrix platform detects global changes in gene expression following acute surgical injury in humans (Wang et al., *Clin Pharmacol Ther* 79:303-315, 2006; Lee et al., *Clin Pharmacol Ther* 79:407-418, 2006) and in rodents following chemotherapy (Dorsey et al., *Biol Res Nurs* 11:7-16, 2009), followed by confirmation for genes of interest with RT-PCR. For the study described below, 2.5 mL of peripheral whole blood was drawn prior to EBRT (baseline), one hour following initiation of EBRT, at day 7, at day 14, at midpoint (day 21), at completion, and four-weeks post EBRT. Fatigue was measured at each time point using a validated questionnaire, the revised Piper Fatigue Scale (rPFS).

Patient Selection

Inclusion criteria of the study included: clinically localized prostate cancer with no prior prostatectomy; scheduled to receive EBRT using Intensity Modulated Radiation Therapy (IMRT) technique that is not anticipated to change during the course of the study; currently receiving androgen deprivation therapy; and no known medical history of tuberculosis.

Patients were excluded if they had progressive or unstable disease of any body system causing clinically significant fatigue including cardiovascular, pulmonary, gastrointestinal, central nervous system, psychiatric, endocrine, hematologic, renal, or immunologic disorders, including patients with any of the following broad disease categories: systemic infections (e.g., human immunodeficiency virus, active hepatitis); if they have documented history of major depression, bipolar disease, psychosis, or alcohol dependence/abuse within the past five years; uncorrected hypothyroidism and anemia; and those with chronic inflammatory disease that may be anticipated to alter the proinflammatory cytokine profile (e.g. rheumatoid arthritis, systemic lupus erythematosus, cirrhosis). Patients taking tranquilizers, steroids, and nonsteroidal anti-inflammatory agents were also excluded because these medications are known to affect cytokine production (Hashioka et al., *Exp Neurol* 206:33-42, 2007; Kato et al., *Schizophr Res* 92:108-115, 2007), as well as patients who have second malignancies or those receiving chemotherapy with their EBRT.

Gene Expression in Peripheral Blood

At every timepoint, about 2.5 mL of peripheral blood was collected using a RNA PAXGene™ collection tube (PreAnalytiX™, Qiagen) for RNA extraction. After incubation for two hours at room temperature, the PAXgene™ tube with peripheral blood was transferred to a −70° C. freezer until ready for RNA extraction. Total RNA was isolated and purified according to the manufacturer's recommendation. The RNA quantity and quality were then analyzed by Nanoprop™ Spectrophotometer (ND-1000) and Experion Electrophoresis Station (Bio-Rad), respectively. Some samples with a lower RNA concentration go through a vacuum centrifugation step to enhance the RNA concentration in order to meet the criteria for microarray synthesis. This process did not affect the RNA quantity and quality for subsequent microarray synthesis.

RNA extraction was processed by the same person following standard operating protocols to minimize non-biological technical bias. The same individual who processed the blood did RNA extraction, purification, cDNA and cRNA synthesis, amplification, hybridization, scanning and data analyses. A total of 100 ng of purified RNA were reverse-transcribed into cDNA using T7-oligo (dT) primer (Affymetrix, Santa Clara, Calif.) and the cDNA was used as a template for transcription. The biotin-labeled cRNA were synthesized from cDNA using 3' IVT Expression kit and followed by purification. A total of 15 μg of fragmented cRNA was hybridized on an Affymetrix GeneChip™ (human U133 plus 2.0) at 45° C. for 16 hours at 60 rpm followed by washing/staining procedures. The U133 plus 2.0 chip is comprised of 54,675 probe sets interrogating 20,317 known human genes. A total of 12,915 probe sets are not well-annotated on the chip. All probe arrays were scanned using GeneChip™ scanner 3000, and Affymetrix GeneChip™ Command Console (AGCC, 3.0 V) was used to scan the images for data acquisition. Raw signal intensity values were obtained for each probe set using the MAS5.0 summarization algorithm.

Statistical Analysis of Gene Expression

Raw signal intensity values were normalized using the S10 transformation algorithm in the MSCL Analyst's Toolbox (developed by Jennifer J. Barb and Peter J. Munson, online at abs.cit.nih.gov/MSCTL Toolbox in JMP Statistical Discovery Software™. The S10 transformation is a variance stabilizing, quantile normalization transform. The S10 values were subjected to a Principal Component Analysis. The transformed data were subjected to a linear regression with respect to the eight time points studied (baseline, day 1, day 7, day 21, day 42, day 48 and day 72). The slope corresponding to the baseline to day 72 was investigated and probe sets passing a 1% False Discovery Rate (FDR) and a slope of 0.09 or greater were chosen.

Fatigue Questionnaire

The rPFS is a 22-item paper/pencil questionnaire that measures 4 fatigue dimensions: behavioral/severity (6 items), sensory (5 items), cognitive/mood (6 items), and affective meaning (5 items) using a 0 to 10 intensity rating scale (0=none; 10=worst intensity). Severe fatigue is defined as a score of ≥6. Psychometric characteristics showed excellent reliability and validity estimates when used in cancer patients. Internal consistency ranged from 0.69 for the symptom dimension to 0.95 for the sensory dimension in cancer patients receiving radiotherapy (Piper et al., *Oncol Nurs Forum* 25:677-684, 1998). The rPFS was administered by a NIH-credentialed clinician with experience in administering this questionnaire in other studies.

Clinical and demographic data (e.g. age, race, stage of prostate cancer, EBRT dose, type of EBRT technique used, laboratory values) were obtained from chart review. All participants were screened for depression using the Hamilton Depression (HAM-D) rating scale, which is a 21-item, clinician-rated paper questionnaire that explores severity of depressive symptoms of the participants in the past week prior to the interview using a 5-point Likert scale (0=none to 4=highest intensity of symptom). When compared to other depression scales, the internal reliability of HAM-D is reported at ≥0.70 with Pearson's r ranging from 0.82 to 0.98. Retest reliability ranged from 0.81 to 0.98; and it was more sensitive to change than the Beck Depression Scale and the Zung Self-Rating Depression Scale. The predefined cut off score for depression is 15 in a cancer study with higher scores indicating higher symptoms of depression (Lydiatt et al., *Arch Otolaryngol Head Neck Surg* 134(5):528-535, 2008).

Example 2

Gene Expression Alterations in CRF

This example describes the identification of 79 genes that are significantly up-regulated or down-regulated in prostate cancer patients receiving radiation therapy and suffering from CRF.

Six patients completed all seven time points of the study. Table 1 describes the demographic and clinical characteristics of the study participants. The mean age of all participants is 59.5 years (±8.2). Five of the six participants had T2 clinical T-stage of their prostate cancer, according to the American Joint Committee on Cancer staging system, $6^{th}$ edition (Campbell et al., *Int J Cancer* 96:198-209, 2001). Fifty percent of patients had Gleason score of 8 while 2/6 had Gleason score of 9. At baseline, all participants had a score of 90 on the Karnofsky Performance Scale which means that they are able to carry out normal activities with minor signs or symptoms of disease. Baseline PSA levels (mean=0.98±0.5) decreased post-EBRT (mean=0.02±0.02). All patients were receiving androgen deprivation therapy 2 months before EBRT; 2/6 had normal testosterone levels (181.0-758.0 ng/dL). Thyroid stimulating hormone (TSH) was within normal range (0.4-4.0 mcIU/mL) for 5/6 participants at baseline, no TSH level was available at baseline for one participant. Hematocrit levels were slightly below normal range (40.1-51.0%) before (mean=39.2±4.0) and at completion (mean=35.5±2.4) of EBRT. Albumin levels were within normal range (3.7-4.7 g/dL) at baseline (mean=4.2+0.2). None of the patients reached the cutoff score for depression at baseline using the HAM-D (mean=3.0+3.4) and none of the depression scores increased at completion of EBRT. All patients received a total dose of 75.6 Gray with IMRT.

TABLE 1

Clinical and demographic characteristics of study participants

| Demographic | Pt 1 | Pt 2 | Pt 3 | Pt 4 | Pt 5 | Pt 6 |
|---|---|---|---|---|---|---|
| Age | 56 | 62 | 49 | 53 | 68 | 69 |
| Ethnicity | AA | C | C | C | C | C |
| Clinical T stage | T3a | T2a | T2c | T2b | T2a | T2b |
| Gleason Score | 8 | 7 | 8 | 8 | 9 | 9 |
| Karnofsky Score | 90 | 90 | 90 | 90 | 90 | 90 |

| Clinical | Normal | Pt 1 | Pt 2 | Pt 3 | Pt 4 | Pt 5 | Pt 6 |
|---|---|---|---|---|---|---|---|
| PSA baseline | 0.00-4.00 mcg/L | 0.32 | 1.75 | 0.85 | 1.34 | 0.32 | 1.28 |
| PSA at completion of EBRT | 0.00-4.00 mcg/L | 0.05 | <0.04 | <0.04 | 0.04 | <0.04 | 0.05 |
| Testosterone, baseline | 181.0-758.0 ng/dL | 32.5 | 459.0 | <20.00 | 23.8 | 327.0 | 23.7 |
| TSH, baseline | 0.40-4.00 mcIU/mL | 0.76 | 3.84 | 3.46 | — | 2.49 | 1.64 |
| Hematocrit baseline | 40.1-51.0% | 38.6 | 41 | 34.4 | 46 | 37.6 | 37.4 |
| Hematocrit at completion | 40.1-51.0% | 36.2 | 35.3 | 32.2 | 39.3 | 36.5 | 33.7 |
| Albumin baseline | 3.7-4.7 g/dL | 3.9 | 4.1 | 4.5 | 4.2 | 4.3 | 4.2 |
| Depression baseline | <15 | 1 | 3 | 8 | 6 | 0 | 0 |
| Depression completion | <15 | 3 | 0 | 0 | 0 | 0 | 0 |
| Total dosage of EBRT (cGy) | | 7560 | 7560 | 7560 | 7560 | 7560 | 7560 |

Pt = Patient; PSA = prostate specific antigen; EBRT = external beam radiation therapy; TSH = thyroid stimulating hormone; cGy = centigray Fatigue Scores All participants complained of fatigue or exhibited increased severity of their fatigue during EBRT. FIG. 1 summarizes the fatigue scores and trends. At baseline, 3/6 of patients with prostate cancer had no fatigue (<1 rPFS score), 1/6 had mild fatigue (1-4 rPFS score), and 2/6 had moderate fatigue (4-6 rPFS score). Fatigue scores peaked on day 14, two weeks after the start of EBRT, in four of the six participants. Fatigue scores of four of the six participants went back to or were lower than baseline levels one month post-EBRT.

Gene Expression Profile

Figure 2:
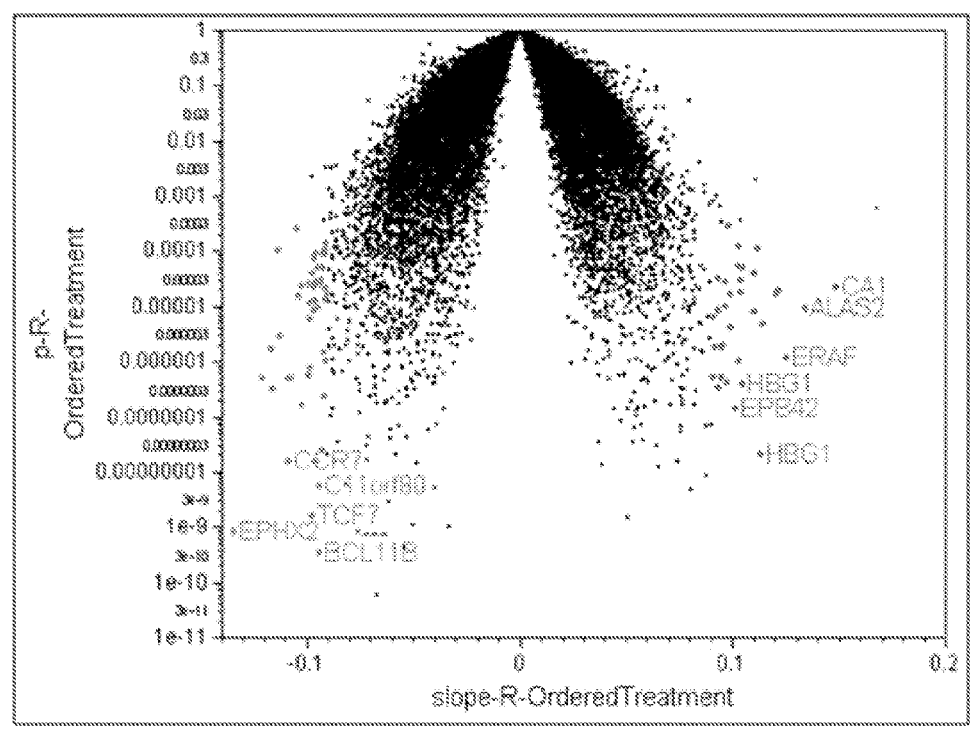
FIG. 2 is a volcano plot showing selection of 79 probe sets using a 1% false discover rate and a slope of 0.09 or greater.
Figure 3:
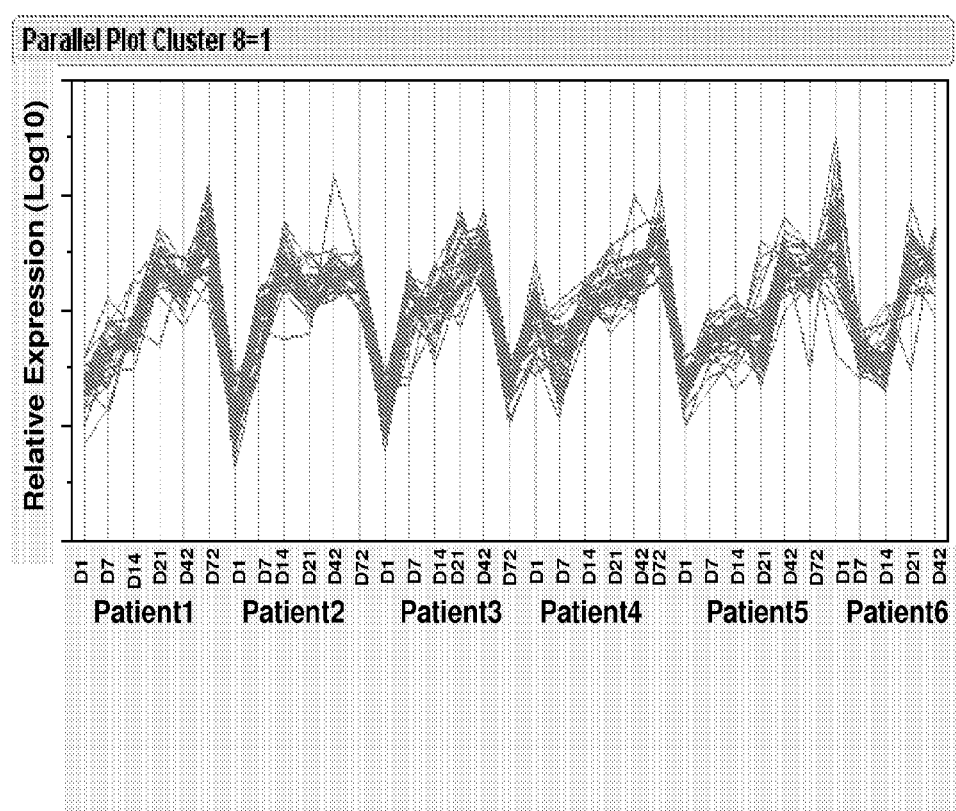
FIG. 3 is a graph of parallel plots of 79 probe sets showing relative expression in six study participants.

During principal component analysis, seven chips were identified as outliers due to technical inconsistencies. With the exception of these outliers and control chips, linear regression analysis was run on remaining 35 gene chips. Seventy nine probe sets were identified after filtering using one percent FDR and a slope of 0.09 or more (over 10-fold, p<0.05) (see FIG. 2), including 61 annotated unique genes. Of these probe sets, there were 10 unannotated probe sets and 13 targeted at least the same gene. Hierarchical clusters of these 79 probe sets revealed two groups of genes that were trending up or down with specific doses of EBRT. Parallel plots of the 79 probe sets show the up and down trend of the unique genes over time beginning with baseline (time 0) through day 72, one month post EBRT (FIG. 3).

Categorizing the 61 annotated genes based on activities revealed six different categories of activities that these genes can be grouped into: (1) iron synthesis, iron integrity or oxygen transport; (2) immune response and inflammatory processes; (3) mitochondrial function and apoptosis; (4) neural transmission; (5) muscle function; and (6) acid-base balance. Table 2 describes these different categories of the 61 annotated unique genes.

TABLE 2

Categories of activities of selected annotated genes

| Cat.* | Gene Symbol | Gene Name | Exp. | Function |
|---|---|---|---|---|
| 1 | SLC4A1 | solute carrier family 4, anion exchanger, member 1 | up | $CO_2$ transport in RBC |
| 1 | HBG1 | hemoglobin, gamma A | up | constitutes hemoglobin |
| 1 | HBD | hemoglobin, delta | up | constitutes hemoglobin |
| 1 | EPB42 | erythrocyte membrane protein band 4.2 | up | RBC integrity |
| 1 | GYPB | glycophorin E; glycophorin B | up | RBC integrity |
| 2 | THEMIS | thymocyte selection pathway associated | down | T-cell antigen receptor signaling |
| 2 | CCR7 | chemokine (C-C motif) receptor 7 | down | mediator of EBV effects on B lymphocytes |
| 2 | TNFRSF25 | tumor necrosis factor receptor superfamily, member 25 | down | stimulates NF-κB activity and regulates cell apoptosis |
| 2 | BCL11B | B-cell CLL/lymphoma 11B (zinc finger protein) | down | translocation may be associated with B-cell malignancies |

TABLE 2-continued

Categories of activities of selected annotated genes

| Cat.* | Gene Symbol | Gene Name | Exp. | Function |
|---|---|---|---|---|
| 2 | MS4A1 | membrane-spanning 4-domains, subfamily A, member 1 | down | development and differentiation of B-cells into plasma cells |
| 3 | SLC6A8 | solute carrier family 6 member 8 | up | transports creatine into and out of cells |
| 3 | FECH | ferrochelatase (protoporphyria) | up | transports creatine into and out of cells |
| 3 | GMPR | guanosine monophosphate reductase | up | catalyzes NADPH-dependent reductive deamination of GMP to IMP |
| 3 | EPHX2 | epoxide hydrolase 2, cytoplasmic | down | converts epoxides to corresponding dihydrodiols |
| 3 | ALAS2 | aminolevulinate, delta-, synt | up | catalyzes the first step in the heme biosynthetic pathway |
| 3 | ARHGEF10 | Rho guanine nucleotide exchange factor (GEF) 10 | down | forms complex G proteins and stimulates Rho-dependent signals |
| 3 | GLRX5 | glutaredoxin 5 | up | involved in the biogenesis of iron-sulfur clusters |
| 3 | AK5 | adenylate kinase 5 | down | regulates adenine nucleotide composition |
| 3 | OSBP2 | oxysterol binding protein 2 | up | inhibits oxysterols' cytotoxicity |
| 3 | SLC25A39 | solute carrier family 25, member 39 | up | mitochondrial carrier protein |
| 3 | ETS1 | v-ets erythroblastosis virus E26 oncogene homolog 1 | down | involved in cell senescence and death |
| 3 | SELM | selenoprotein M | down | signals translation termination |
| 3 | SNRPN | small nuclear ribonucleoprotein polypeptide N | down | plays a role in pre-mRNA processing |
| 3 | OGT | O-linked N-acetylglucosamine (GlcNAc) transferase | down | encodes glycosyltransferase that competes with phosphorylation |
| 3 | DEAD | DEAD (Asp-Glu-Ala-Asp) box polypeptide 17 | | involved in processes altering RNA secondary structure |
| 4 | SNCA | synuclein, alpha (nonA4 amyloid precursor) | up | integrates presynaptic signaling and membrane trafficking |
| 4 | XK | X-linked Kx blood group (McLeod syndrome) | up | associated with neuromuscular and hematopoietic dysfunction |
| 4 | APBA2 | amyloid B precursor protein-binding, family A, member 2 | down | involved in signal transduction processes |
| 4 | NSUN5C | NOL1/NOP2/Sun domain family, member 5C | down | deletion associated with Williams Beuren Syndrome |
| 4 | SELENBP1 | selenium binding protein 1 | up | deficiency of selenium may cause certain neurologic diseases |
| 4 | SOX8 | SRY (sex determining region Y)-box 8 | down | involved in brain development and function |
| 4 | CASK | calcium/calmodulin-dependent serine protein kinase | down | encodes protein located at brain synapses |
| 4 | OR2W3 | olfactory receptor, family 2, subfamilies T2, members 8&3 | up | responsible for recognition of olfactory signals |
| 4 | TNS1 | tensin 1 | up | crosslink filaments involved in signal transduction |
| 5 | MYL4 | myosin, light chain 4, alkali; atrial, embryonic | up | myosin alkali light chain in embryonic muscle and adult atria |
| 6 | NR3C2 | nuclear receptor subfamily 3, group C, member 2 | down | mediates aldosterone actions on salt and water balance |
| 6 | CA1 | carbonic anhydrase I | up | involved in reversible hydration of carbon dioxide |

*Categories: 1 = Iron synthesis/RBC integrity/oxygen delivery; 2 = Immune response/inflammation; 3 = Mitochondrial function/apoptosis; 4 = Neural transmission; 5 = Muscle function; 6 = Acid-base balance

Discussion

The results disclosed herein demonstrate that some of the genes that were significantly expressed during radiotherapy are related to the physiological mechanisms proposed to be causing CRF. Moreover, these results suggest a relationship exists between genes expressed following EBRT and fatigue scores. The unbiased approach of this study revealed findings that have functional significance to mechanisms of radiation-induced fatigue.

The physiological mechanisms of CRF are based on limited evidence that genetic factors, energy expenditure, metabolism, aerobic capacity, and the individual's immune response to inflammation are responsible for the experience of CRF. From the mitochondrial standpoint, CRF could be due to attenuated physiological and cellular energy caused by a reduction in the capacity of mitochondria to utilize oxygen and synthesize adenosine triphosphate (ATP) (Eghbal et al., *Toxicology* 203(1-3):69-76, 2004; Lemle, *Med Hypotheses* 72(1):108-109, 2009). Mitochondrial dysfunction is involved in clinical conditions associated with defective oxidative phosphorylation in energy metabolism which can cause an overall dysfunction of the mitochondrial electron transport chain (ETC) or can be associated with single or multiple defects in the five ETC-related complexes including NADH-ubiquinone oxidoreductase, succinate dehydrogenase-CoQ oxoreductase, cytochrome reductase, cytochrome oxidase, and ATP synthase (Mandelker, *Vet Clin North Am Small Anim Pract* 38(1):1-30, 2008).

One of the genes that was identified in this study as significantly overexpressed is alpha-synuclein. Overexpression of α-synuclein has been associated in patients with progressive neurodegeneration leading to dementia, parkinsonism, and other behavioral impairments (Olivares et al., *Int J Mol Sci* 10:1226-1260, 2009). Fibrillar aggregates of α-synuclein are noted as cytoplasmic inclusions of dopaminergic neurons and non-dopaminergic neurons including glial cells and axonal spheroids (Duda et al, *J Neuro sci Res* 61(2):121-127, 2000). A case report of one patient with pathologic triplication of α-synuclein suffered from fatigue for two years before being diagnosed with Parkinson's disease (Singleton et al., *Brain* 127:768-772, 2004). Overexpression of α-synuclein generates immunopositive cellular inclusions and causes mitochondrial impairments through increased production of reactive oxygen species (Hsu et al., *Am J Pathol* 157(2):401-410, 2000), lysosomal dysfunction (Stefanis et al., *J Neurosci* 21(24): 9549-9560, 2001), and Golgi apparatus fragmentation (Gosavi et al., *J Biol Chem* 277(50): 48984-48992, 2002) leading to cell death.

Several other significantly over- or under-expressed genes were identified in the study disclosed herein that are associated with neural signaling and transmission (X-linked Kx; amyloid B precursor protein binding, family A, member 2), synaptic trafficking (calcium/calmodulin-dependent serine protein kinase, tensin 1) and brain development (sex determining region Y-box 8).

Another gene of special interest is the human creatine transporter gene (SLC6A8). This gene encodes specific creatine transporters that allow absorption of phosphocreatine, an important energy buffer and energy transducer in the heart, brain, and skeletal muscles (Wallimann et al., *Biochem J* 281:21-40, 1992). SLC6A8 is expressed in most tissues but highest in skeletal muscles and kidney and lowest in colon, brain, heart, testis, and prostate (Nash et al., *Receptors Channels* 2:165-174, 1994). Defects in SLC6A8 gene caused by hemizygous nonsense mutation produce a delay in speech and language development, hypotonia, and extrapyramidal movement abnormalities. These abnormalities respond well with exogenous creatine supplementation. Muscle weakness linked to SLC6A8 gene mutation is characterized by ptosis and myopathic facies which is believed to have a cerebral origin (Salomons et al., *Am J Hum Gen* 68:1497-1500, 2002; Hahn et al., *Am J Hum Gen* 70:1349-1356, 2002). No prior studies have explored the etiology of the muscle abnormality related to SLC6A8 gene defect.

There is currently no optimal pharmacologic therapy for CRF because its etiology is unknown. Without knowing the etiology of CRF, interventional options to manage CRF will remain challenging. Identification of biomarkers for CRF at clinically significant time points following cancer treatment provides necessary information on therapeutic targets and optimal timing to manage CRF.

Example 3

Verification of Gene Expression Changes in 16 Prostate Cancer Patients

This example describes a validation study that demonstrated that SNCA, TNFRSF25, SLC6A8 and ARHGEF10 were differentially expressed in RNAs from 16 patients. Two of the four genes (SNCA and SLC6A8) were significantly correlated to fatigue scores ($p<0.001$).

Procedures
Global Gene Expression

At every timepoint, about 8.5 mL of peripheral blood sample was collected; 2.5 mL using a RNA PAXgene™ collection tube (PreAnalytiX™, Qiagen) for RNA extraction and 6 mL using an EDTA tube. The PAXgene™ tube with peripheral blood was transferred immediately after collection to a −80° C. freezer until ready for RNA extraction. Total RNA from the study participants were age-, gender-, and race-matched with RNA from healthy controls. The RNAs from study participants and healthy controls were isolated and purified according to the manufacturer's recommendation. The RNA quantity and quality were then analyzed by Nanoprop™ Spectrophotometer (ND-1000) and Experion Electrophoresis Station (Bio-Rad), respectively. Some samples with a lower RNA concentration went through a vacuum centrifugation step to enhance the RNA concentration in order to meet the criteria for microarray synthesis. This process did not affect the RNA quantity and quality for subsequent microarray studies.

The RNA extraction, purification, cDNA and cRNA synthesis, amplification, hybridization, scanning and data analyses were conducted following standard operating protocols to minimize non-biological technical bias. A total of 100-200 ng of purified RNA were reverse-transcribed into cDNA using T7-oligo (dT) primer (Affymetrix, Santa Clara, Calif.) and the cDNA was used as a template for transcription. The biotin-labeled cRNA were synthesized from cDNA using 3' IVT Expression kit, followed by purification. A total of 15 µg of fragmented cRNA were hybridized on Affymetrix GeneChip™ (human U133 plus 2.0) at 45° C. for 16 hours at 60 rpm followed by washing/staining procedures. The U133 plus 2.0 chip is comprised of 54,675 probe sets interrogating 20,317 known human genes. A total of 12,915 probe sets are not well-annotated on the chip. All probe arrays were scanned using GeneChip™ scanner 3000, and Affymetrix GeneChip™ Command Console (AGCC, 3.0 V) was used to scan the images for data acquisition. Raw signal intensity values were obtained for each probe set using the MAS5.0 summarization algorithm.

Confirmation by Real-Time PCR

A confirmatory real time PCR was performed using $RT^2$ First Strand Kit to make cDNA. This was prepared by using a genomic DNA elimination mixture (25.0 ng to 5.0 µg+2 µl 5× gDNA Elimination Buffer+$H_2O$ to final volume of 10 µl) which was incubated at 42° C. for 5 minutes, and then immediately chilled on ice for one minute. RT cocktail was then prepared for 9 reactions (36 µl 5×RT Buffer 3, 9 µl Primer and External Control Mix, 18 µl RT Enzyme Mix 3, and 27 µl $H_2O$). First Strand cDNA synthesis reaction was performed by adding 10 µl of RT cocktail to each 10 µl Genomic DNA Elimination Mixture, which was immediately incubated at 42° C. for exactly 15 minutes, then the reaction was immediately stopped by heating at 95° C. for 5 minutes. 91 µl of $H_2O$ was then added and mixed to each cDNA synthesis reaction (20 µl). The cDNA was placed on ice or in −20° C. until polymerase chain reaction. The diluted cDNA template quality was then analyzed using the Nanoprop™ Spectrophotometer (ND-1000). Four genes with highest fold change (SNCA, TNFRSF25, ARHGEF10, SCL6A8) were followed at all timepoints and two housekeeping genes (GAPDH, ACTB) were used. RNAs from study participants were age-, gender-, race-matched from healthy controls using 384-well optical plates using an ABI PRISM™ 7900 HT sequence detection system (Applied Biosystems, Foster City, Calif.).

To ensure uniformity in PCR efficiency and amplification conditions, the Real-Time $RT^2$ qPCR Primer Assay (Catalog No. C-03/330401, SABiosciences, Frederick, Md.) was used. The plate was filled by adding 1 µl of diluted cDNA (diluted with dH$_2$O 1:1) and master mixes made up of 5 µl RT$^2$ Real Time SYBR Green/Rox PCR Master Mix (Catalog No. PA-0, 2-12, SA Biosciences, Foster City, Calif.), 3.6 µl dH$_2$O, and 0.4 µl of specified primer pair were added to each well. All samples were tested in triplicates. After the samples were added, the plate was sealed and vortexed followed by centrifugation for 2 minutes at 2300 rpm. The 384-well optical plate was placed into the ABI PRISM™ 7900 HT sequence detection system were two-step cycling program was analyzed.

Results
Gene Expression Profile

During principal component analysis, seven chips were identified as outliers due to technical inconsistencies. With the exception of these outliers and control chips, linear regression analysis was run on the remaining 88 gene chips. One hundred two probe sets were identified after filtering using one percent FDR and a slope of 0.09 or more (over 10-fold, $p<0.05$), including 61 annotated unique genes. Of these probe sets, there were 10 unannotated probe sets and 13 targeted at least the same gene. Hierarchical clusters of these 79 probe sets revealed two groups of genes that were trending up or down with specific doses of EBRT. Parallel plots of the 102 probe sets show the up and down trend of the unique genes over time beginning with baseline (time 0) through day 72, one month post EBRT.

Categorizing the 61 annotated genes based on activities revealed six different categories of activities that these genes can be grouped into: iron synthesis, iron integrity or oxygen transport; immune response and inflammatory processes; mitochondrial function and apoptosis; neural transmission; acid-base balance; and muscle function.

Real Time Polymerase Chain Reaction (rtPCR)

Four differentially expressed genes (TNFRSF25, ARHGEF, SCL6A8, SNCA) were selected for rtPCR confirmation based on the results of the pathway analyses. GAPDH and ACTB were used as housekeeping genes during the confirmatory rtPCR. These four genes were fitted into four linear mixed effects models for analyses. Using fold changes (ΔΔCT) of the genes analyzed, there were no significant differences in gene expression of the four genes between the prostate cancer patients and their matched controls at baseline. However, the fatigue scores are significantly associated with the gene expression levels of all four genes (TNFRSF25 $p=0.002$, ARHGEF10 $p=0.007$, SCL6A8 $p=0.010$, SNCA $p=0.008$) overtime before, during, and after EBRT. Using cycle number, all the other genes changed significantly over time (SNCA $p<0.001$, ARHGEF10 $p=0.02$, SCL6A8 $p<0.001$) except for TNFRSF25. The fatigue scores were significantly correlated with the gene expression levels of SNCA ($p<0.001$) and SLC6A8 ($p<0.001$).

Example 4

Cancer Treatment-related Fatigue is Associated with SNCA Overexpression

This example describes microarray data obtained from 20 subjects with prostate cancer receiving EBRT. A significant correlation was found between fatigue scores and SNCA expression over time during EBRT.

Methods

Men with non-metastatic prostate cancer were enrolled in this study. Patients with any of the following were excluded: progressive disease causing significant fatigue; psychiatric disease within five years; uncorrected hypothyroidism and anemia; taking sedatives, steroids, and non-steroidal anti-inflammatory agents; and with second malignancies.

Fatigue was measured at each time point using the revised Piper Fatigue Scale (rPFS), using a zero to ten rating scale (zero=none; ten=worst intensity) (Piper et al., *Oncol Nurs Forum* 25:677-684, 1998). Outcomes were measured at baseline (prior to EBRT, DO); one hour following initiation of EBRT (D1), day 7 (D7), day 14 (D14), at midpoint (days 19-21, D21), at completion (days 38-42, D42), and four weeks post EBRT (days 68-72, D72).

Gene Expression Chip Processing and Pathway Analysis

At each time point, 2.5 mL of blood from each subject was collected using RNA PAXGene™ tubes (Qiagen, Frederick, Md.). The collected blood was stored frozen (−80° C.) until ready for RNA extraction. RNA extraction, purification, cDNA and cRNA synthesis, amplification, hybridization, scanning and data analyses were conducted following standard protocols as previously described (Wang et al., *Pain* 128:136-147, 2007). A total of 80 Affymetrix microarray chips (HG U133 Plus 2.0, Santa Clara, Calif.) were summarized using Affymetrix GeneChip™ Command Console (AGCC, 3.0 V). Raw signal intensity values were normalized using the S10 transformation algorithm from the MSCL Analyst's Toolbox. S10 transformation is a variance stabilizing, quantile normalization transform and is scaled to match a base 10 logarithm. S10 values were subjected to principal component analysis in order to detect outliers. Seven chips were identified as outliers and excluded from further analysis. The remaining transformed data were subjected to linear regression analysis adjusted for patient effect with respect to the seven time points treated as equal intervals. The slope measured the trend of expression change between baseline through D72.

Ingenuity Pathway analysis (Ingenuity® Systems, Redwood City, Calif.) identified functional networks of the differentially expressed probesets from the Ingenuity's Knowledge Base. Right-tailed Fisher's exact test was used to calculate p-values determining the probability that each biological function and/or disease assigned to these networks is due to chance alone.

Confirmatory qPCR

To confirm differential SNCA expression, qPCR was performed using SYBR Green I dye (Foster City, Calif.). Total RNA was isolated with PAXgene™ blood RNA kit and treated with DNase I during purification. First strand cDNA was synthesized using RT$^2$ First Strand Kit (Qiagen, Frederick, Md.) with 100 ng of total RNA and subsequently diluted ten-fold with dH$_2$O. Q-PCR amplification mixers (10 µl) contained one µl of diluted first strand cDNA, ten µl of 2×RT$^2$ Real Time SYBR Green/Rox PCR Master Mix (Qiagen, Frederick, Md.) and 400 nM of forward and reverse primers. Reactions were carried on ABI PRISM 7900HT Sequence Detection System and were subjected to an initial ten minute denaturation at 95° C. and 40 cycles at 95° C. for 15 seconds and 60° C. for 60 seconds.

Five potential reference genes were tested including B2M (beta-2-microglobulin), HPRT1 (hypoxanthine phosphoribosyltransferase 1), RPL13A (ribosomal protein L 13a), GAPDH (glyceraldehydes-3-phosphate dehydrogenase) and ACTB (actin, beta). GAPDH and ACTB were validated and chosen as reference genes. Efficiencies of GAPDH (reference position 1287), ACTB (reference position 1222) and SNCA (reference position 876) primers were between 90% and 110%. When calculating for ΔCt values, geometric means of Ct values of the 2 reference genes were used. Mitochondrial genes were quantified using the 84-gene profile from the human mitochondria RT$^2$ profiler PCR Array System (SA-Biosciences, Frederick, Md.).

Confirmation by ELISA

Whole blood collected using EDTA tubes were centrifuged and cells were separately stored at −80° C. Alpha-synuclein cell lysate levels were quantified using human α-synuclein ELISA kits (Invitrogen, Camarillo, Calif.). Cell pellets were thawed on ice and lysed in 2 volumes of cell extraction buffer (10 mM Tris HCl, pH7.4, 100 mM NaCl, 1 mM EDTA, 1 mM EGTA, 1% Triton, 0.1% SDS and 10% glycerol with protease inhibitors) for 30 minutes with vortexing at ten minute intervals. After centrifugation at 13,000 rpm for ten minutes at 4° C., the supernatant was transferred to fresh tubes and diluted 1:10 in standard diluent buffer. ELISA was performed using 50 μl of diluted cell lysate according to the manufacturer's guide. The plates were read in a microplate reader VICTOR$^3$ at 450 nm. All samples were tested in triplicate.

Statistical Methods

Descriptive statistics were calculated for the participants' demographic characteristics. Linear regression, linear mixed effect models taking patient as a random effect and the study time points as the fixed effect and correlation analyses were conducted using the JMP Statistical Discovery Software™ and a package of scripts (MSCL Toolbox). Correlation between microarray and qPCR data was calculated using averaged S10SG values over 5 microarray probesets and averaged delta CT values over 9 patients at each time point. Correlation between qPCR and ELISA data was calculated over 12 patients at each time point using averaged delta CT values and averaged α-synuclein cell lysate values (ng/mg). Correlation between qPCR and ELISA data with averaged raw fatigue scores was calculated over 16 patients.

Results

Twenty patients completed all seven time points of the study and 20 age-, gender-, and race-matched controls with no prostate cancer were used to compare baseline gene and protein expression data of study participants. Table 3 describes the demographic and clinical characteristics of the study participants. The mean age of all participants is 62.7 years (±7.9), which is within ±5 years from the matched controls (58.5±10.8). Six of the participants had a T2a clinical T-stage of their prostate cancer, four had a T1c stage, and the rest had a T2b to T3c stage (N=10/20) (Campbell et al., *Int J Cancer* 96:198-209, 2001). Six patients (37%) had a Gleason score of 9, and 14 patients had Gleason scores from 6 to 8. At baseline, 19 participants had a score of 90 on the Karnofsky Performance Scale indicating that they were able to carry out normal activities with minor signs or symptoms of disease, while one had a score of 80 which indicates that the participant is able to carry normal activities but show some signs or symptoms of the disease. Seventeen patients (85%) received androgen deprivation therapy two months before EBRT and three patients had radical prostatectomy more than 6 months before scheduled to receive EBRT. At baseline, testosterone levels ranged from 20 to 505 ng/dL with a mean of 264.4 ng/dL (normal=181.0-758.0 ng/dL). Thyroid stimulating hormone (TSH) (range=0.17-3.84 mcIU/mL; normal=0.4-4.0 mcIU/mL) and albumin levels were normal (range=2.7-4.5 g/dL; normal=3.7-4.7 g/dL). Baseline PSA levels (mean=21.2±27.4) decreased post-EBRT (mean=0.1±0.3) and hematocrit levels, which were normal at baseline (mean=40.5±3.5; normal=40.1-51.0%) decreased at completion of EBRT (mean=36.8±2.8). None of the patients reached the cutoff score for depression using the Hamilton Depression Scale (HAM-D) at baseline (mean=1.2±2.3) and at completion of EBRT (mean=2.0±2.5). Eighty five percent (N=17/20) of patients received a total dose of 75.6 Gray with IMRT, while the remaining 3/20 received a total dose of 68.4 Gray.

TABLE 3

Clinical and demographic characteristics of sample

| Characteristics | Subjects-Baseline (n = 20) | Subjects-Completion (n = 20) | Controls (n = 20) | Normal Range |
|---|---|---|---|---|
| Age (in years), mean (range) | 63 (49-74) | | 58 (48-84) | |
| Race, n (%) | | | | |
| Caucasian | 13 (65.0) | | 13 (65.0) | |
| African American | 4 (20.0) | | 4 (20.0) | |
| Others | 3 (15.0) | | 3 (15.0) | |
| Body Mass Index, mean (SD) | 30.4 (5.0) | | 27.8 (2.7) | |
| Testosterone, mean (SD) | 264.4 (159.6) | | | 181.0-758.0 ng/DL |
| Thyroid Stimulating Hormone, mean (SD) | 2.0 (1.4) | | 2.0 (1.7) | 0.4-4.0 μIU/mL |
| Albumin, mean (SD) | 3.9 (0.4) | | 4.0 (0.3) | 3.7-4.7 g/dL |
| Depression, mean (SD) | 1.2 (2.3) | 2.0 (2.5) | | |
| Hematocrit, mean (SD) | 40.5 (3.5) | 36.8 (2.8) | | 40.1-51.0% |
| Prostate Specific Antigen, mean (SD) | 21.2 (27.4) | 0.1 (0.3) | | 0.0-4.0 μg/L |
| Clinical T stage, n (%) | | | | |
| T1c | 4 (20.0) | | | |
| T2a | 6 (30.0) | | | |
| T2b | 2 (10.0) | | | |
| T2c | 4 (20.0) | | | |
| T3a | 2 (10.0) | | | |
| T3b | 1 (5.0) | | | |
| T3c | 1 (5.0) | | | |
| Gleason Score, n (%) | | | | |
| 6 | 4 (20.0) | | | |
| 7 | 6 (30.0) | | | |

TABLE 3-continued

Clinical and demographic characteristics of sample

| Characteristics | Subjects-Baseline (n = 20) | Subjects-Completion (n = 20) | Controls (n = 20) | Normal Range |
|---|---|---|---|---|
| 8 | 4 (20.0) | | | |
| 9 | 6 (30.0) | | | |
| Karnofsky Score, mean (SD) | 89.5 (2.2) | | | |

Fatigue During EBRT

Figure 4:
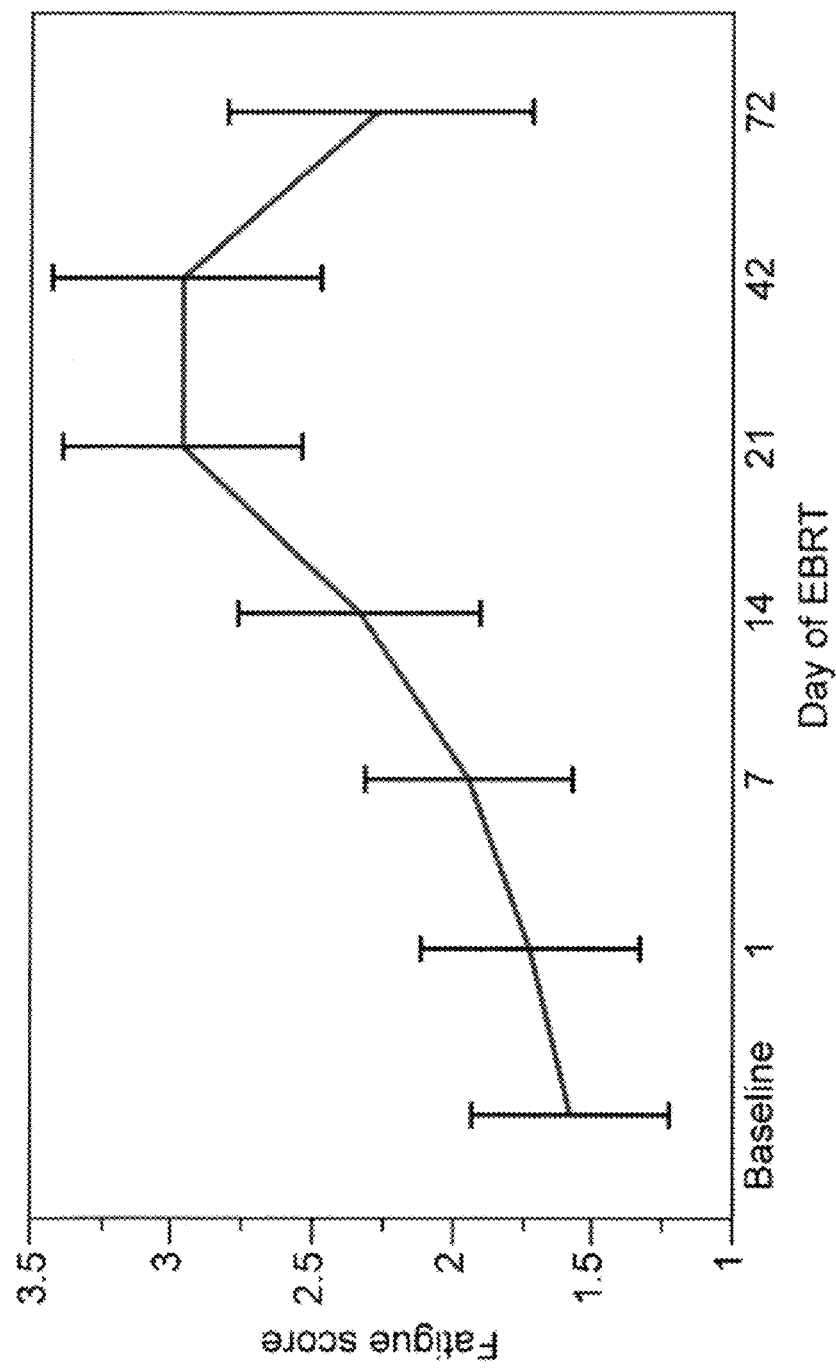
FIG. 4 is a line graph showing average fatigue score versus 7 time points. Standard error bars are ±1 standard error from the mean. Mean fatigue score was taken over 20 patients. The p-value generated (p<0.00001) from a linear mixed effect model analysis (see methods).

The fatigue scores of participants were measured at each time point using the revised Piper Fatigue Scale (rPFS), a 22-item paper/pencil questionnaire which defines severe fatigue as a score of ≥6 (Wang et al., Pain 128:136-147, 2007). The mean fatigue score of all participants increased significantly over time (p<0.0001) during EBRT (FIG. 4). Compared to the baseline fatigue scores (mean=1.6±1.6), the mean fatigue scores significantly increased at midpoint of EBRT (mean=3.0±1.9, p<0.001), continued to be significantly higher at completion of treatment (mean=3.0±2.1, p=0.002), but showed no significant difference between baseline scores and one month post-EBRT (mean=2.3±2.4, p=0.14). High variability in mean fatigue scores were observed with each participant at each time point. Similarly, there was a high variability in the change of fatigue scores with each participant over time during EBRT.

Gene Expression by Microarray

Gene expression profile from white blood cells of subjects collected during EBRT was conducted using microarray analysis. Four hundred sixty three probesets (178 upregulated and 285 down regulated) were differentially expressed over time after the probesets passed filtering criteria of 1% false discovery rate (FDR) and a slope of 0.07 or more (over 2.6-fold change, p<0.0003). Table 4 below shows the 10 most upregulated and 10 most downregulated genes identified in the microarray analysis. Expression values represent the fold change in expression at D21 compared to baseline on a log 10 scale.

Figure 5:
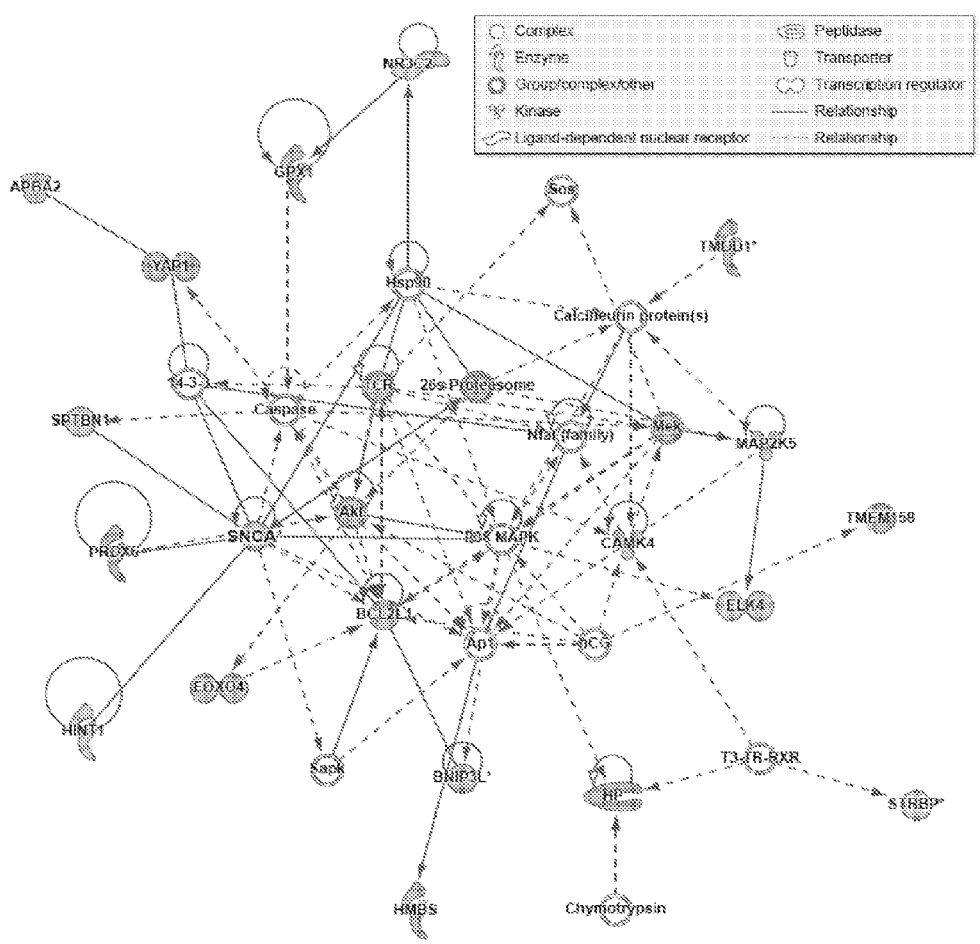
FIG. 5 is a schematic showing the results of pathway analysis based on the microarray data set.
Figure 6A:
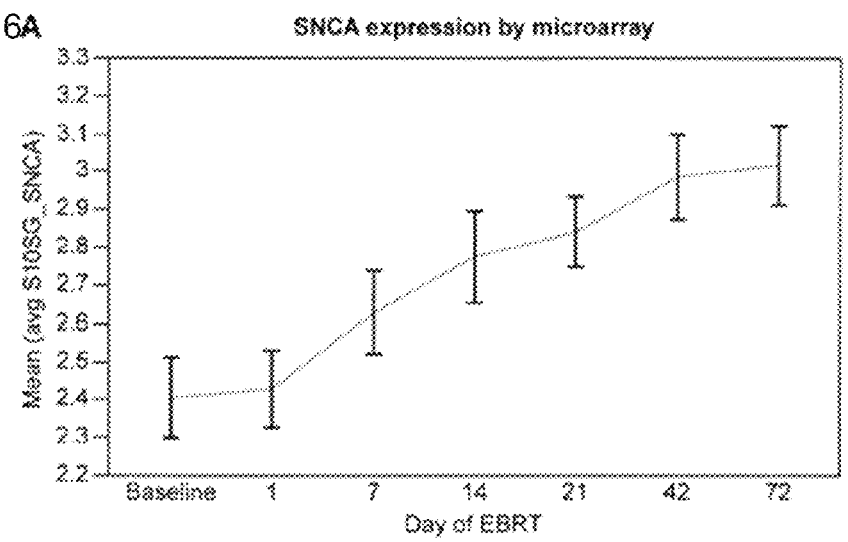
FIGS. 6A-6C are line graphs showing expression of SNCA. (A) Average S10SG (Avg-S10SG_SNCA) expression over 5 probesets versus 7 time points. Standard error bars are ±1 standard error from the mean. Mean value taken over 9 patients. The p-value generated (p<0.0001) from a linear mixed effect model analysis (see methods). (B) Average negative log 2 fold change of 6 time points compared to baseline in qPCR. Standard error bars are ±1 standard error from the mean. Mean taken over 16 patients. The p-value is generated from a linear mixed effect model analysis. (C) Average cell lysate (ng/mg) versus 7 time points. Standard error bars are ±1 standard error from the mean. Mean taken over 16 patients. The p-value is generated from a linear mixed effect model analysis.

SNCA, the α-synuclein gene, had a 2.95-fold change in expression at D21 compared to baseline or an expression value of 0.47 on a log 10 scale, making this gene one of the highly upregulated genes. The average log 10 expression over five SNCA probesets over patients was plotted over time during EBRT (FIG. 6A), where a significant upward trend of SNCA expression was noted (p<0.0001). Pathway analysis identified the networks from the Ingenuity® Pathway Analysis library that were most significant to the 463 differentially expressed probesets in the microarray data set (FIG. 5). SNCA is positioned centrally in the Ingenuity® networks identified. The canonical pathways related to SNCA overexpression during EBRT using Ingenuity® revealed pathways related to 14-3-3-mediated signaling, which is involved in phosphorylation-dependent protein-protein interactions (Wilker and Yaffe, J Mol Cell Cardiol 37:633-642, 2004), Huntington's disease, and Parkinson's signaling.

Confirmation of α-synuclein Expression During EBRT

Figure 6B:
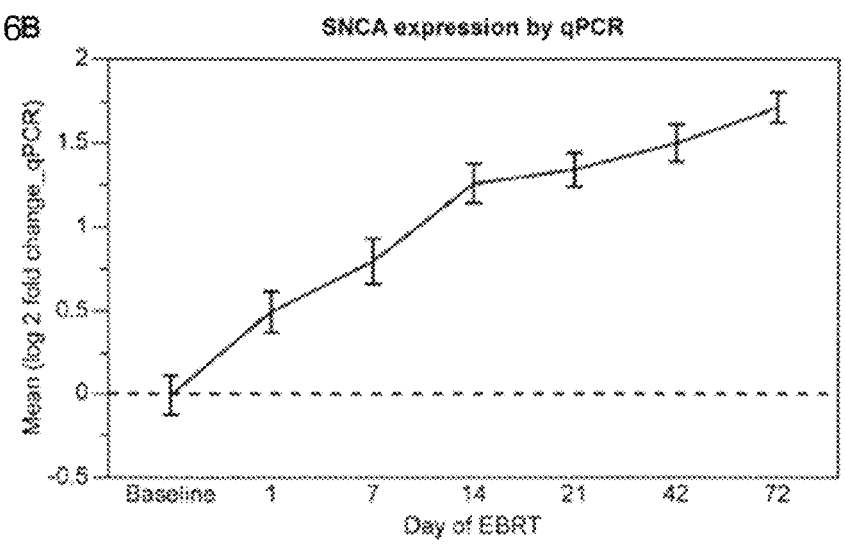
Figure 6C:
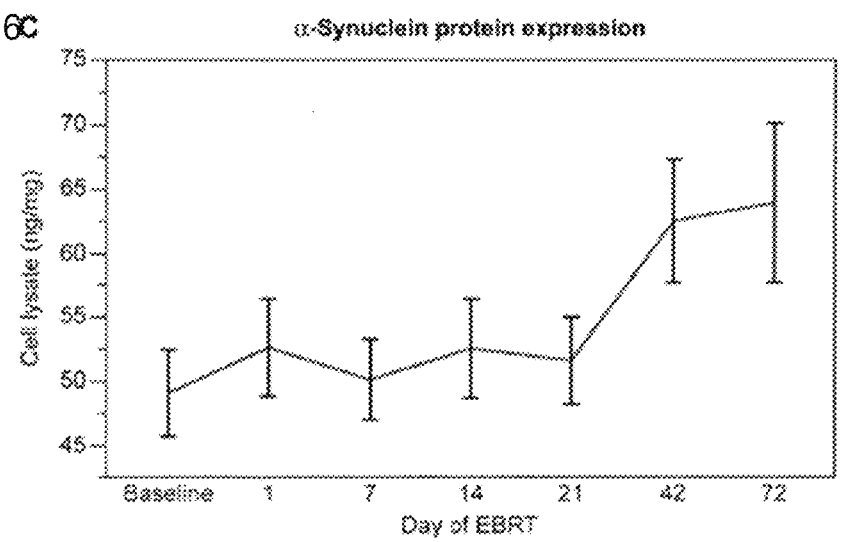

A confirmatory quantitative PCR (qPCR) was performed from white blood cells to measure the expression of SNCA using GAPDH and ACTB as reference genes. There was no significant difference between the baseline values for participants and matched controls (p=0.78). A significant change of SNCA expression during EBRT was observed using average negative log 2 fold change of 6 time points compared to baseline (FIG. 6B, p<0.0001). Similarly, a significant change in expression of the α-synuclein protein from cell lysates of subjects collected during EBRT was also observed (FIG. 6C, p<0.0001).

TABLE 4

Top upregulated and downregulated genes

| Upregulated Genes | | | Downregulated Genes | | |
|---|---|---|---|---|---|
| Gene Symbol | Gene Name | Expression Value | Gene Symbol | Gene Name | Expression Value |
| IFI27 | Interferon alpha-inducible protein 27 | 0.774 | MS4A1 | B-lymphocyte antigen CD20 | −0.821 |
| CA1 | Carbonic anhydrase 1 | 0.705 | IGHM | Ig mu chain C region | −0.816 |
| HBD | Hemoglobin subunit delta | 0.640 | PAX5 | Paired box protein Pax-5 | −0.791 |
| XK | X-linked Kx blood group | 0.534 | FCRLA | Fc receptor-like A | −0.669 |
| HBG2 | Hemoglobin subunit gamma-2 | 0.513 | TTC3 | Tetratricopeptide repeat protein 3 | −0.647 |
| RHCE/RHD | Blood group Rh(CE) polypeptide | 0.507 | NSUN5C | NOP2/Sun domain family, member 5C | −0.642 |
| AHSP | Alpha hemoglobin stabilizing protein | 0.496 | POU2AF1 | POU domain class 2-associating factor 1 | −0.636 |
| GYPB | Glycophorin B | 0.483 | CCR7 | C-C chemokine receptor type 7 | −0.632 |
| SNCA | Alpha synuclein | 0.470 | FAIM3 | Fas apoptotic inhibitory molecule 3 | −0.613 |
| ISCA1 | Iron-sulfur cluster assembly 1 homolog | 0.464 | BLK | B lymphoid tyrosine kinase | −0.612 |

Correlation Between α-synuclein mRNA and Protein Expression

Figure 7B:
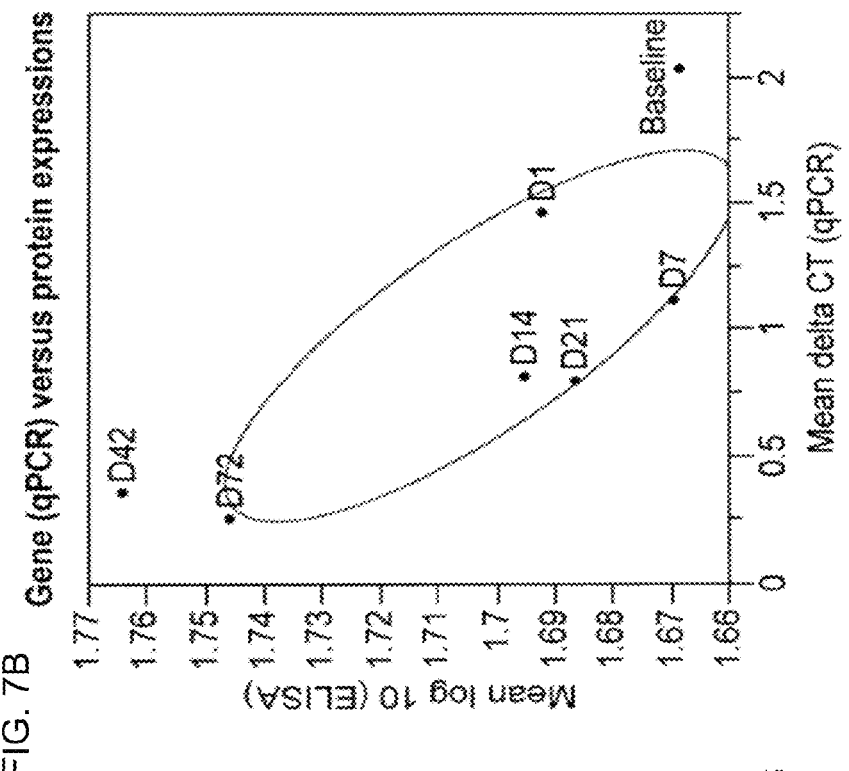
FIGS. 7A and 7B are graphs showing the correlation between $\alpha$-synuclein mRNA and protein expression in EBRT patients. (A) Correlation on average delta CT versus average S10SG of SNCA gene for each of 7 time points. Average taken over 16 patients for each time point. The density ellipse is computed from the bivariate normal distribution fit to the X and Y variables with p=0.5 (JMP statistical software). R=−0.96, p<0.0005. (B) Correlation on average cell lysate versus average delta CT for each of 7 time points. Average taken over 16 patients for each time point. The density ellipse is computed from the bivariate normal distribution fit to the X and Y variables with p=0.5 (JMP statistical software). R=−0.80, p<0.03.
Figure 7A:
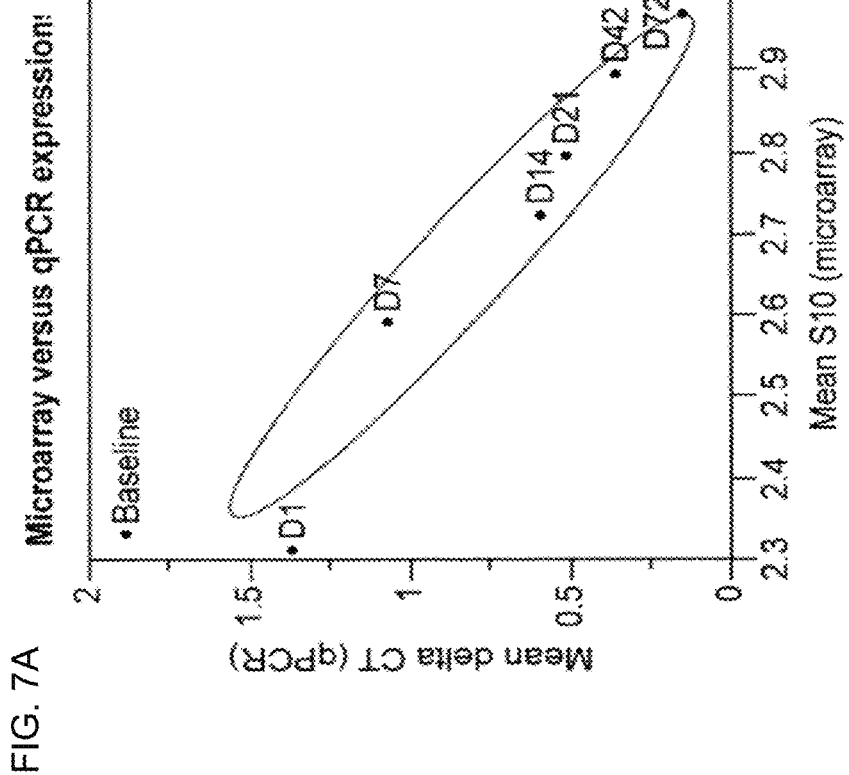

SNCA expression measured by microarray was strongly correlated with SNCA expression measured in qPCR (FIG. 7A, R=−0.96, p=0.0005). Similarly, a significant correlation was also noted between the mean SNCA expression by qPCR and α-synuclein protein expression over time during EBRT (FIG. 7B, R=−0.80, p=0.03). This significant correlation between the gene and protein levels confirms the differential expression of α-synuclein over time during EBRT.

Correlation Between Fatigue Scores and α-synuclein Expression

Figure 8A:
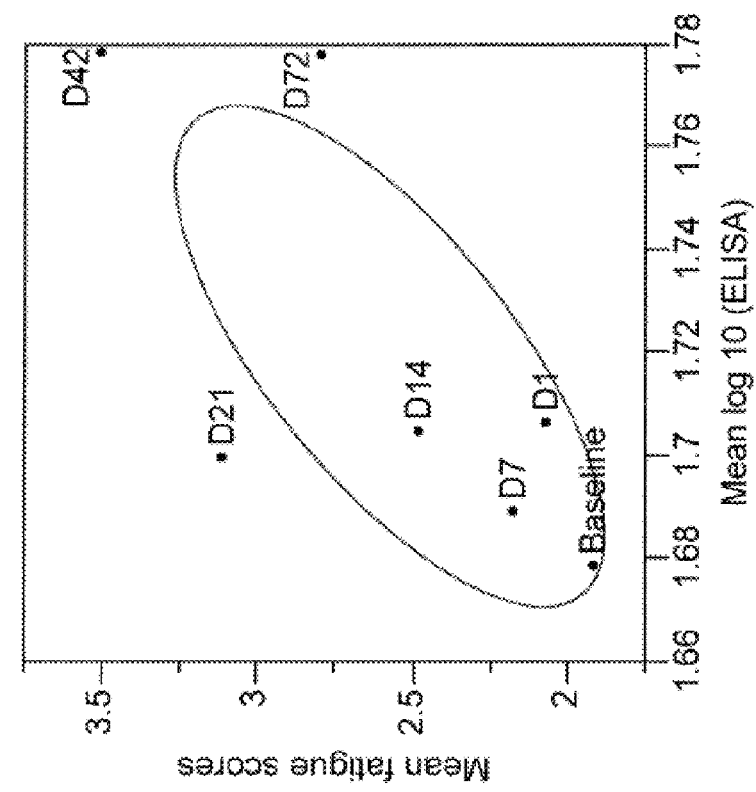
FIGS. 8A and 8B are graphs showing the correlation between SNCA expression and fatigue. (A) Correlation on average delta CT versus average fatigue score for each of 7 time points. Average taken over 16 patients for each time point. The density ellipse is computed from the bivariate normal fit to the X and Y variables with p=0.5 (JMP statistical software). R=−0.90, p<0.006. (B) Correlation on average cell lysate versus average fatigue score for each of 7 time points. Average taken over 16 patients for each time point. The density ellipse is computed from the bivariate normal distribution fit to the X and Y distribution variables with p=0.5 (JMP statistical software). R=−0.72, p=0.07.
Figure 8B:
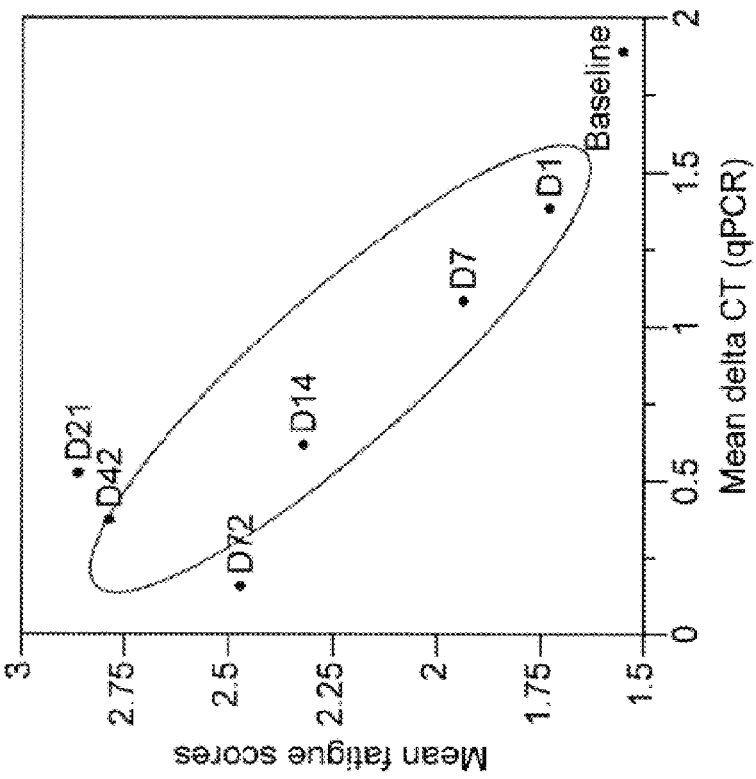

The mean fatigue scores and mean SNCA expression by qPCR at each time point was correlated (FIG. 8A, R=−0.90, p=0.006). In addition, a correlation between the mean fatigue scores and mean α-synuclein protein expression over time during EBRT was also observed (FIG. 8B, R=0.72, p=0.07).

Discussion

The studies described in the Examples herein are the first to demonstrate differential expression of novel genes that are significantly associated with changes in fatigue symptoms of men with non-metastatic prostate cancer receiving localized radiation therapy. One of the most differentially expressed genes was SNCA which encodes the α-synuclein protein known to form inclusions in dopaminergic and non-dopaminergic neurons (Musgrove et al., *Neurotox Res.* 19:592-602, 2011), causing mitochondrial impairments and enhancing cellular oxidative stress (Hsu et al., *Am J Pathol* 157:401-410, 2000), leading to neurodegeneration (Hashimoto et al., *Neuroreport* 10:717-721, 1999), as seen in dementia, Parkinsonism, and other behavioral impairments (Olivares et al., *Int J Mol Sci* 10:1226-1260, 2009). Pathway analysis of the differentially expressed genes in this study indicates a central role of SNCA.

Alpha-synuclein is expressed as a physiologic response to intrinsic or external insults to serve as a neuroprotective mechanism against subsequent attacks (Musgrove et al., *Neurotox Res.* 19:592-602, 2011). Previous studies confirm that elevated level of the α-synuclein protein in cellular cytoplasm is a measure of resilience against oxidative stress and cellular protection from toxic insults (Hashimoto et al., *J Biol Chem* 277:11465-11472, 2002; Manning-Bog et al., *J Neurosci* 23:3095-3099, 2003; Monti et al., *J Neurochem* 103:518-530, 2007). Alpha-synuclein is observed as a molecular chaperone to many physiologic proteins such as the muscarinic receptors (Leng et al., *J Biol Chem* 276:28212-28218, 2001), and the SNARE proteins (Burre et al., *Science* 329:1663-1667, 2010). Its expression is induced as a physiological response to EBRT; however, its physiological effects might be muted by the expression of other mechanisms involved in the physiological response to injury related to the radiation therapy, causing a decrease in reported fatigue 30 days post EBRT, even if α-synuclein expression continues to increase post treatment.

Without knowing the molecular-genetic etiology of CRF, interventional options to manage CRF have been challenging. Identification of biomarkers for CRF provides insight on therapeutic targets to manage CRF. Determining the functional significance of the association between fatigue symptoms and α-synuclein expression may also identify other key nodal pathways that may provide explanations to the mechanisms behind CRF.

Example 5

Mitochondria-related Gene Expression Changes are Associated with Fatigue in Patients with Non-Metastatic Prostate Cancer Receiving EBRT This example describes a study to evaluate changes in expression of genes related to mitochondrial function. In this study, 11 genes related to mitochondrial function were differentially expressed in prostate cancer patients receiving EBRT, eight of which (AIFM2, BCL2, FIS1, IMMP2L, MSTO1, SLC25A23, SLC25A37, SLC25A4) were significantly associated with fatigue scores.

Patients and Methods

Study Samples and Recruitment

This exploratory study used prospective and repeated measures designed to assess fatigue in men with non-metastatic prostate cancer prior to EBRT at 7 time points: day 0 (baseline), day 1 of EBRT, day 7, day 14, day 19-21 (midpoint of EBRT), day 38-42 (completion of EBRT), and day 68-72 (30 days post EBRT). Baseline data obtained from study subjects (n=15) were compared with data obtained from age-, gender-, and race-matched controls without prostate cancer (n=15) for a total of 30 subjects.

Inclusion criteria included males ≥18 years of age, clinical diagnosis of localized prostate cancer, scheduled to receive EBRT using IMRT technique, concurrently receiving androgen deprivation therapy (ADT), and able to provide written informed consent. Patients were ineligible if they had progressive or unstable disease of any body system causing clinically significant fatigue, systemic infections (e.g., human immunodeficiency virus, active hepatitis), documented history of major depression, bipolar disorder, psychosis, or alcohol dependence/abuse within the past 5 years, uncorrected hypothyroidism or anemia, second malignancies, concurrent chemotherapy with their EBRT, and those with chronic inflammatory disease that may alter proinflammatory cytokine profiles (e.g., rheumatoid arthritis, systemic lupus erythematosus, cirrhosis). Additionally, patients taking sedatives, steroids, or non-steroidal anti-inflammatory agents were excluded because these medications are known to affect immunogenetic changes (Hashioka et al., *Exp Neurol* 206:33-42, 2007; Kato et al., *Schizophr Res* 92:108-115, 2007).

Measures/Instruments

Demographic and clinical characteristics of study participants (e.g., age, ethnicity, stage of disease, prostate specific antigen (PSA), testosterone, hematocrit, and albumin values) were retrieved by chart review. Data on demographic and clinical characteristics were collected once at baseline. Participants were screened for depression using the Hamilton Depression Rating Scale (HAM-D), a 21-item, clinician-rated paper questionnaire with good internal reliability (α=0.81 to 0.98) (Hamilton, *J Neurol Neurosurg Psychiatry* 23:56-62, 1960). Data were collected on the HAM-D at each of the 7 time points. The pre-defined cut-off score for depression is 15 in cancer patients, with higher scores indicating more symptoms of depression (Lydiatt et al., *Arch Otolaryngol Head Neck Surg* 134:528-535, 2008).

Fatigue was measured by the validated revised Piper Fatigue Scale (rPFS), which is a 22-item paper/pencil, self-administered questionnaire that measures four dimensions of fatigue (behavioral/severity, sensory, cognitive/mood, and affective) using a 0 to 10 intensity rating scale (0=none; 10=worst intensity). Data were collected at each of the 7 time points. Scores were categorized as mild fatigue (1-3), moderate fatigue (4-5), and severe fatigue (>6). The rPFS has demonstrated reliability and validity when used in cancer patients receiving radiation therapy with internal consistency ranging from 0.69 for the symptom dimension to 0.95 for the sensory dimension (Piper et al., *Oncol Nurs Forum* 25:677-684, 1998).

Gene Expression in Peripheral Blood

Peripheral blood samples (2.5 mL) were collected from each subject at each of the 7 time points using PAXgene™ blood ribonucleic acid (RNA) tubes (PreAnalytiX, Hombrechtikon, Ohio) to explore changes in gene expression related to mitochondrial biogenesis and function. The collection tubes with peripheral white blood cells were inverted 10 times to ensure red blood cell lysis immediately after collection, and the samples were immediately stored at −80° C. until RNA extraction. RNA extractions were processed by a single laboratory technician following a standard protocol to minimize non-biological technical bias. Total RNA extraction, cDNA synthesis, amplification, and data analyses were performed according to manufacturer's procedure. Total RNA was isolated and extracted from frozen whole blood samples following the Paxgene™ blood RNA kit procedure (PreAnalytiX, Hombrechtikon, Ohio). RNA yields were ≥3 μg from each 2.5 mL of whole blood collected. All extracted RNA was purified using RNeasy™ mini kit (Qiagen, Valencia, Calif.). Total RNA concentration, purity, and integrity were tested using the Nanoprop™ (ND-1000, Wilmington, Del.) and Experion systems (Biorad, Hercules, Calif.). Following RNA preparation, the samples were treated with DNase to ensure elimination of genomic DNA. A total of 100 to 150 ng of extracted RNA per sample were then converted to cDNA using the $RT^2$ First Strand Kit (SABiosciences, Frederick, Md.). After cDNA synthesis reaction, the cDNA was diluted using nuclease-free $H_2O$ and immediately stored at −20° C. until used for human mitochondria-related gene expression profiling.

Real-Time PCR Array for Mitochondria-Related Gene Expression

The Human Mitochondria $RT^2$ Profiler PCR Array System (PAHS-087A, SABiosciences, Frederick, Md.) was used to evaluate gene expression profiles of 84 genes involved in mitochondrial biogenesis and function. The genes evaluated in this PCR Array include 10 groups of mitochondrial regulators and mediators related to membrane polarization and potential, mitochondrial transport, small molecule transport, targeting proteins to mitochondria, mitochondrial protein import, outer membrane translocation, inner membrane translocation, mitochondrial fission and fusion, mitochondrial localization, and mitochondrial apoptotic genes. Diluted first strand cDNA was mixed with 2× SABiosciences $RT^2$ qPCR master mix (SABiosciences, Frederick, Md.). Ten μL of PCR cocktail was added to each well of the 384-well PCR array for real-time PCR detection. The real time PCR was carried out using the ABI PRISM® 7900HT Real Time PCR System. SYBR™ Green fluorescence was detected from each well during the annexing step of each cycle through the real-time thermal cycler program.

Statistical Analyses

Descriptive statistics were used to describe demographic/clinical characteristics of sample, fatigue scores and changes in gene expression at each time point. An independent t-test was used to compare differences in fatigue scores and changes in gene expression between patients and controls at baseline. A mixed linear effects model was used to describe the changes in gene expression and fatigue scores over time and to determine the association between changes in gene expression and fatigue scores at each time point. All statistical analyses were conducted using the Statistical Analysis System (SAS) version 12.0 (SAS Institute Incorporated, Cary, N.C.). Power analysis calculated using study that reported significant difference in fold changes of gene expression and fatigue scores (Bower et al., Brain Behav Immun 25:147-150, 2011), suggested a minimum of 10 subjects were needed to obtain 90% power at p<0.05 significance level.

PCR data were analyzed using the $\Delta\Delta C_t$ method (PCR Array Data Analysis Web Portal, SABiosciences Corp., Qiagen, Frederick, Md.). At least 3 reference genes (RPL13A, GAPDH, ACTB) were selected for normalization of data. Genes with more than a 2-fold change in gene expression and p-value<0.05 at any time point during EBRT were considered as significant up- or down-regulation in gene expression. For Ingenuity pathway analysis (IPA), genes with more than a 1.5-fold change and p-value<0.05 at Day 14, Day 21, Day 42 or Day 72 were included.

Results

Sample Demographics

Fifteen patients with non-metastatic prostate cancer undergoing EBRT and 15 age-, gender-, and race-matched controls were enrolled in the study (Table 5). The mean age of the subjects (62.8±8.6) was within ±5 years from the mean age of matched controls (57.2±7.6). More than half (n=9/15) of the participants had stage T2 (a-c) prostate cancer with Gleason scores (range=6-9) and baseline PSA levels (range=0.61-111 mcg/L) that were consistent with intermediate to high risk progression of the disease. All participants were receiving neoadjuvant therapy with ADT 8 weeks before starting EBRT. Baseline thyroid stimulating hormone (mean=1.8±1.2 mcIU/mL), testosterone (mean=243.9±159.9 ng/dL), albumin (mean=4.1 g/dL±0.3), and hematocrit (mean=40.3%±3.8) were within normal ranges (thyroid stimulating hormone=0.4-4.0 mcIU/mL, testosterone=181-758 ng/dL, albumin=3.7-4.7 g/dL, hematocrit=40.1-51%, respectively). None of the participants reached the cutoff score for depression (HAM-D) either at baseline or at the end of EBRT. Of the 15 subjects with prostate cancer, 13(87%) received a total of 42 fractions with 75.6 Gy using the IMRT technique.

TABLE 5

Description of sample demographics and clinical characteristics

| | Subjects (N = 15) | | | | Controls (N = 15) | | | | Normal |
|---|---|---|---|---|---|---|---|---|---|
| | Mean | SD | Range | N (%) | Mean | SD | Range | N (%) | Range |
| Age in Years | 62.8 | 8.6 | 49-81 | 15 (100) | 57.2 | 7.6 | 45-76 | 15 (100) | |
| Ethnic | | | | | | | | | |
| Caucasian | | | | 10 (67) | | | | 10 (67) | |
| African-American | | | | 3 (20) | | | | 3 (20) | |
| Others | | | | 2 (13) | | | | 2 (13) | |
| Clinical T Stage | | | | | | | | | |
| T1 (a-c) | | | | 2 (13) | | | | | |
| T2 (a-c) | | | | 9 (60) | | | | | |
| T3 (a-c) | | | | 4 (27) | | | | | |

TABLE 5-continued

Description of sample demographics and clinical characteristics

| | Subjects (N = 15) | | | | Controls (N = 15) | | | | Normal |
|---|---|---|---|---|---|---|---|---|---|
| | Mean | SD | Range | N (%) | Mean | SD | Range | N (%) | Range |
| Gleason score (median) | 8 | 1 | 6-9 | | | | | | |
| Kamofsky score | 89.3 | 2.6 | 80-90 | | | | | | |
| BMI | 30.4 | 5.2 | 22.9-40.7 | | | | | | |
| Depression | | | | | | | | | |
| Baseline | 1.5 | 2.6 | 0-8 | | | | | | |
| Completion | 2.3 | 2.6 | 0-8 | | | | | | |
| PSA Level (ng/mL) | | | | | | | | | 0.0-4.0 |
| Baseline | 23.2 | 27.5 | 0.61-111 | | | | | | |
| Completion | 0.04 | 0.01 | 0.04-0.05 | | | | | | |
| Hematocrit (%) | | | | | | | | | 40.1-51.0 |
| Baseline | 40.3 | 3.8 | 32.9-46.9 | | | | | | |
| Completion | 36.8 | 2.9 | 33.0-42.0 | | | | | | |
| Albumin Levels (g/dL) | | | | | | | | | 3.7-4.7 |
| Baseline | 4.1 | 0.3 | 3.5-4.5 | | | | | | |
| Testosterone (ng/dL) | | | | | | | | | 181-758 |
| Baseline | 243.9 | 159.9 | 20-505 | | | | | | |
| TSH (mcIU/mL) | | | | | | | | | 0.4-4.0 |
| Baseline | 1.8 | 1.2 | 0.17-3.8 | | | | | | |
| Total dosage of EBRT (Gray) | | | | | | | | | |
| 75.6 | | | | 13 (87) | | | | | |
| 68.4 | | | | 2 (13) | | | | | |

Abbreviations: BMI, body mass index; dl, deciliter; EBRT, external beam radiation therapy; g, gram; mcl, microliter; ml, milliliter; ng, nanogram; PSA, prostrate specific antigen; TSH, thyroid stimulating hormone Fatigue Score Mean fatigue scores were 1.66 (SD=1.66) at baseline (pre-EBRT) for patients and 0.67 (SD=1.2) for controls. There was no significant difference in fatigue scores at baseline between patients and controls (p=0.09). The mean fatigue score increased to 3.06 (SD=1.95) at midpoint of EBRT, slightly decreased to 2.98 (SD=2.20) at completion of EBRT, and remained slightly elevated at 30 days post EBRT 2.64 (SD=2.56). However, there was a significant change in fatigue score over time during EBRT compared to baseline data (p=0.00-0.04) for the sample.

Mitochondria-Related Gene Expression

Figure 9:
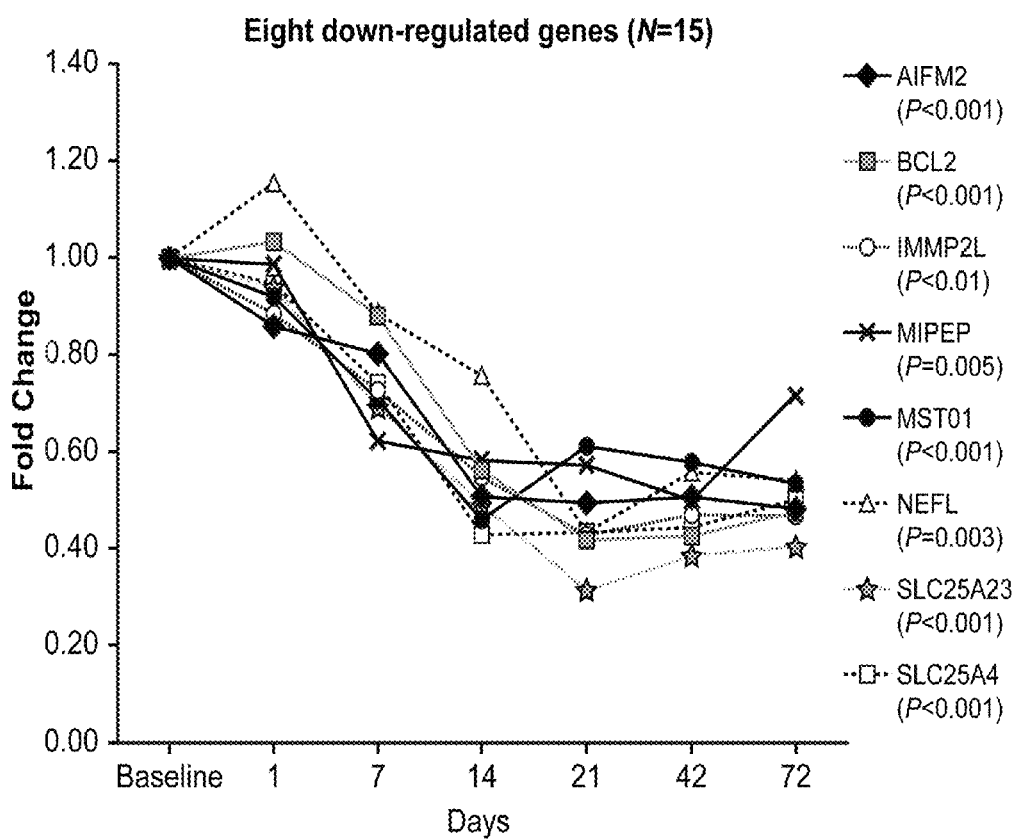
FIG. 9 is a graph showing the decrease in expression over time during EBRT compared to baseline for eight genes associated with mitochondrial function. The genes included apoptosis-inducing factor mitochondrion associated 2 (AIFM2), B-cell CLL/lymphoma 2 (BCL-2), IMP 2 inner mitochondrial membrane peptidase-like (IMMP2L), mitochondrial intermediate peptide (MIPEP), misato homolog 1 (Drosophila) (MSTO1), neurofilament, light polypeptide (NEFL), solute carrier family 25 member 23-mitochondrial carrier, phosphate carrier (SLC25A23), and solute carrier family 25 member 4-mitochondrial carrier, and adenine nucleotide translocator (SLC25A4).
Figure 10:
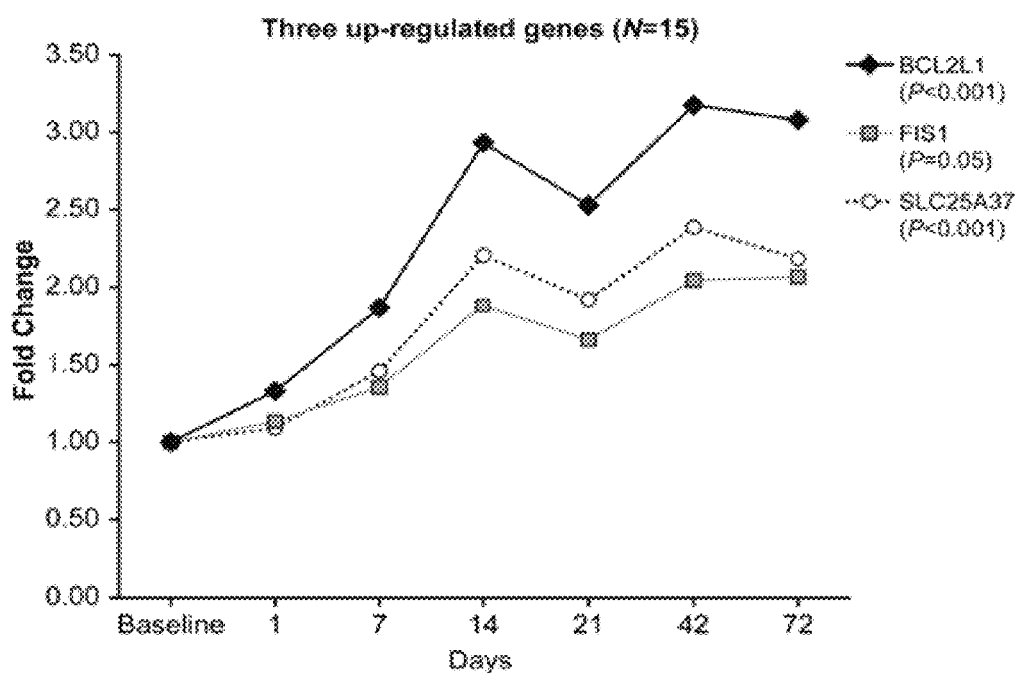
FIG. 10 is a graph showing the increase in expression over time during EBRT compared to baseline for three genes associated with mitochondrial function. The genes included BCL2-like 1 (BCL2L1), fission 1 (FIS1) and solute carrier family 25, member 37 (SLC25A37).

There was no significant difference in mitochondria-related gene expression at baseline between patients and controls (p=0.07-0.86). Eleven genes related to mitochondrial function were differentially expressed over time during EBRT compared to baseline (p<0.05). Three of the 11 genes (BCL2L1, FIS1, SLC25A37) were greater than 2.5-fold up-regulated (FIG. 10) and 8 of the 11 genes were greater than 2-fold down-regulated (FIG. 9). These 8 down-regulated genes included the apoptosis-inducing factor mitochondrion associated 2 (AIFM2), B-cell CLL/lymphoma 2 (BCL-2), IMP 2 inner mitochondrial membrane peptidase-like (IMMP2L), mitochondrial intermediate peptide (MIPEP), misato homolog 1 (Drosophila) (MSTO1), neurofilament, light polypeptide (NEFL), solute carrier family 25 member 23-mitochondrial carrier, phosphate carrier (SLC25A23), and solute carrier family 25 member 4-mitochondrial carrier, adenine nucleotide translocator (SLC25A4). Table 6 summarizes each of these 11 differentially expressed mitochondrial related genes and their functions. There were 25 genes in the array showing at least 1.5-fold changes in expression (p=0.00-0.05) at different time points (day 14, day 21, day 42 and day 72).

Eight of the 11 differentially expressed genes were significantly associated with fatigue scores (AIFM2, BCL-2, FIS1, IMMP2L, MSTO1, SLC25A23, SLC25A37, and SLC25A4). Table 7 indicates the association between fatigue and mitochondrial related genes. The 25 genes with more than a 1.5-fold change in expression at a p-value of <0.05 at Day 14, Day 21, Day 42 or Day 72 were subjected to pathway analysis using IPA. The following functional networks related to the differential expression of the 25 genes were noted: cellular morphology, cellular assembly and organization and cell death.

TABLE 6

Expression changes of 11 mitochondria-related genes and their functions

| Symbol | (↑)/(↓) | Fold Change/ P value[a] | Full Gene Name | Function |
|---|---|---|---|---|
| BCL2L1 | (↑) | 1.33-3.17/ .0007-.0421 | BCL2-like 1 | Anti-or Pro-apoptosis; Potent inhibitor of cell death |
| FIS1 | (↑) | 1.13-2.07/ .0002-.0481 | Fission 1 (mitochondrial outer membrane) homolog (S. cerevisiae) | Regulates the morphology of mitochondria via balancing between fission and fusion In mitochondria |

TABLE 6-continued

Expression changes of 11 mitochondria-related genes and their functions

| Symbol | (↑)/(↓) | Fold Change/ P value[a] | Full Gene Name | Function |
|---|---|---|---|---|
| SLC25A37 | (↑) | 1.09-2.39/ .0012-.0197 | Solute carrier family 25 (mitochondrial carrier; adenine nucleotide translocator), member 37 | Localized in the mitochondrial inner membrane; an essential iron importer for the synthesis of mitochondrial heme and iron-sulfur clusters |
| AIFM2 | (↓) | 0.86-0.49/ .0002-.0030 | the apoptosis-inducing factor mitochondrion associated 2 | Oxidoreductase, mediating a TP53/p53-dependent apoptosis response. A caspase-independent mitochondrial effector of apoptotic cell death |
| BCL2 | (↓) | 1.03-0.42/ .0005-.0222 | B-cell CLL/lymphoma 2 | Proto-oncogene; Suppresses apoptosis in a variety of cell systems |
| IMMP2L | (↓) | 0.89-0.43/ .0001-.0372 | IMMP2L, IMP2 | Catalyzes the removal of transit peptides required for the targeting of proteins from the mitochondrial matrix, across the inner membrane, into the inter-membrane space |
| MIPEP | (↓) | 0.99-0.50/ .0065-.0233 | Mitochondrial intermediate peptidase | Cleaves proteins, imported into the mitochondrion, to their mature size |
| MSTO1 | (↓) | 0.92-0.46/ .0025-.0299 | Misato homolog 1 (*Drosophila*) | Localized to the mitochondrial outer membrane; has a role in mitochondrial fission, distribution, and morphology |
| NEFL | (↓) | 1.16-0.43/ .0458-.0702 | Neurofilament, light polypeptide | Neurofilaments, are involved in the maintenance of neuronal caliber |
| SLC25A23 | (↓) | 0.94-0.32/ .0001-.0002 | Solute carrier family 25 (mitochondrial carrier; phosphate carrier), member 23 | Calcium-dependent mitochondrial solute carrier |
| SLC25A4 | (↓) | 0.95-0.43/ .0003-.0131 | Solute carrier family 25 (mitochondrial carrier; adenine nucleotide translocator), member 4 | Catalyzes the exchange of ADP and ATP across the mitochondrial inner membrane |

[a] represents range of fold-changes and p-values for comparison of gene expression at each of 7 post-radiation time points with baseline. Gene expressions related to mitochondria were evaluated using real-time PCR via the RT[2] ProfileR PCR Array System for 15 patients at baseline and 6 post-radiation time points. The table lists the genes with >2 fold up- or down-regulation changes or P-value <.05 for at least one post-radiation time point compared with baseline.

TABLE 7

Association between fold changes of mitochondria-related genes and fatigue scores using mixed linear effects model

| | Fatigue Score | |
|---|---|---|
| Mitochondrial Related Gene | Beta (β) | Non-Adjusted P Value |
| AIFM2[b] | −1.26 | .006 |
| BCL2[b] | −1.30 | .0002 |
| BCL2L1 | 0.10 | .22 |
| FIS1[b] | 0.51 | .02 |
| IMMP2L[b] | −1.56 | .0002 |
| MIPEP | −0.73 | .06 |
| MSTO1[b] | −1.71 | .0003 |
| NEFL | −2.22 | .21 |
| SLC25A23[b] | −1.08 | .002 |
| SCL25A37[b] | 0.43 | .012 |
| SLC25A4[b] | −0.77 | .028 |

[b] gene expression change is significantly associated with fatigue score

Discussion

This is the first study to explore relationships between expression changes of genes related to mitochondrial integrity/function and self-reported fatigue in men with non-metastatic, localized prostate cancer receiving EBRT. Results from this hypothesis-generating study using an unbiased approach indicate a significant relationship between changes in expression of 8 mitochondrial-related genes and fatigue in this population.

More than 90% of ATP is produced by mitochondrial oxidative phosphorylation through two coordinated metabolic processes—the tricarboxylic acid (TCA) cycle, and the electron transport/respiratory chain (ETC) (Pieczenik and Neustadt, *Exp Mol Pathol* 83:84-92, 2007). The mitochondrial ETC is critical for maintaining effective ATP levels (Mandelker, *Vet Clin North Am Small Anim Pract* 38:1-30, 2008), suggesting that a contributor to fatigue could be caused by a reduction in the capacity of mitochondria to utilize oxygen and synthesize ATP (Eghbal et al., *Toxicology* 203:69-76, 2004; Lemle, *Med Hypotheses* 72:108-109, 2009). It has been hypothesized that the inability of mitochondria to produce a sufficient supply of energy in the form of ATP plays a major role in fatigue (Lemle, *Med Hypotheses* 72:108-109, 2009). The results disclosed herein support this hypothesis by demonstrating that 11 genes associated with mitochondrial integrity and functions critical to ATP production were differentially expressed during EBRT. Eight of these 11 differentially genes are directly involved in mitochondrial apoptosis pathway and signaling (AIFM2, BCL2, BCL2L1), mitochondrial membrane polarization and potential (BCL2, BCL2L1), mitochondrial transport (BCL2, BCL2L1, IMMP2L, MIPEP), and small molecular transport (SLC25A23, SLC25A37, SLC25A4).

The solute carrier family 25 (SLC25) consists of proteins that are coding for mitochondrial transporters. The SLC25 family proteins transport molecules (ATP/ADT, amino acids, malate, ornithine, citruline) from macromolecules to mitochondria to be converted into energy through oxidative phosphorylation (Haitina et al., *Genomics* 88:779-790, 2006). Three differentially expressed genes (SLC25A4, SLC25A23, SLC25A37) found in this study are linked with SLC25 family proteins that not only trigger cellular injuries but speed cellular death through disturbance in energy supply. For example, SLC25A4 encodes the ADP/ATP translocator or adenine nucleotide translocator (ANT), which is the most abundant mitochondrial protein. The ANT determines the rate of ADP/ATP flux between the mitochondrion and the cytosol and regulates oxidative energy metabolism in cells. ANT dysfunction (up- or down-regulated) is related to the pathogenesis of metabolic syndromes (Kim et al., *Korean Diabetes J* 34:146-153, 2010). Secondly, Mitoferrin-1 (Mfrn 1; SCL25A37) is located in the mitochondrial inner member and functions as an essential iron importer for the synthesis of mitochondrial heme and iron-sulfur cluster in erythroblasts (Chen et al., *Proc Natl Acad Sci USA* 106:16263-16268, 2009). Lastly, SCL25A23 is a novel human member of the mitochondrial solute carrier (MSC) proteins, which encode the human isoforms of the ATP-Mg/Pi carrier in mitochondria and mediate the transport of metabolites across the inner mitochondrial membrane (Bassi et al., *Gene* 345:173-182, 2005). This is the first report that explores changes in gene expression of SCL25A37 or SCL25A23 in a human model. The findings disclosed herein indicate that over expression of SCL25A37 and down-regulation of SCL25A23 and SLC25A4 are associated with fatigue symptoms because heme transport and oxidative energy metabolism are impaired in this population.

Radiation-induced free radicals ($O_2^-$, $OH^-$, $ONO_2^-$) frequently cause oxidative damage including the accumulation of defective proteins, increased mutation rates of mitochondrial DNA, impairment of mitochondrial metabolism, and initiation of the mitochondrial/intrinsic pathway of apoptosis (Wallace, *Annu Rev Genet.* 39:359-407, 2005; Sheridan et al., *Molecular Cell* 31:570-585, 2008). The intrinsic apoptosis pathway is often activated in response to cell stress or damage such as those caused by radiation. It is regulated by the interaction of bcl-2 family members in the mitochondria (Sheridan and Martin, *Mitochondrion* 10:640-648, 2010). Activation of pro-apoptotic bcl-2 family members during intrinsic cell death leads to the formation of pores in mitochondrial outer membranes, followed by release of cytochrome C and other pro-apoptotic factors from the mitochondrial intermembrane space into the cytosol (Youle and Strasser, *Nat Rev Mol Cell Biol* 9:47-59, 2008), and then trigger a conformational change to permit the apoptosome of caspase activation (Logue and Martin, *Biochem Soc Trans* 36:1-9, 2008).

The data presented herein confirm the differential expression of genes linked with cell death as evidenced by the up-regulation of BCL2L1 and down-regulation of BCL2 and AIFM2, which are responsible for maintaining mitochondrial membrane integrity and resisting apoptosis. Differential expression of these genes (BCL2L1, BCL2, AIFM2) causes an imbalance in the interaction among bcl-2 proteins leading to failure to inhibit BAX oligomerization. Impairing this cascade may lead to increased mitochondrial outer membrane permeability, and consequently impair ability to release cytochrome C to resist apoptosis (Teijido and Dejean, *FEBS Lett* 584:3305-3310, 2010). The present findings indicate that down-regulation of BCL2 and AIFM2 are associated with self-reported fatigue experienced by non-metastatic prostate cancer patients receiving EBRT.

The study disclosed herein demonstrates that genes related to mitochondria and their function are not only differently expressed during EBRT, but are also significantly related to the changes in fatigue symptoms reported by patients with non-metastatic prostate cancer during EBRT.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of diagnosing and treating a subject with cancer-related fatigue (CRF), comprising:
   detecting expression of SNCA and IFI27 in a sample obtained from the subject;
   comparing expression of SNCA and IFI27 in the subject to a control;
   diagnosing the subject with CRF if an increase in expression of SNCA and IFI27 relative to the control is detected; and
   providing an appropriate to the subject.

2. The method of claim 1, wherein expression of SNCA and IFI27 is increased at least 2-fold, at least 3-fold, at least 4-fold or at least 5-fold relative to the control.

3. The method of claim 1, further comprising detection expression of one or more genes SLC25A37, BCL2L1, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10 in a sample obtained from the subject;
   comparing expression to one or more of SLC25A37, BCL2L1, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6A8, OR2W3, MYL4, TNFRSF25, OGT, APBA2, CASK, IL7R, ITGA6 and ARHGEF10 in the subject to a control; and
   diagnosing the subject with CRF if an increase in expression of SLC25A37, BCL2L1, CA1, HBD, XK, HBG2, RHCE/RHD, AHSP, GYPB, ISCA1, SLC6A8, OR2W3 or MYL4, or a decrease in expression of MS4A1, IGHM, PAX5, FCRLA, TTC3, NSUN5C, POU2AF1, CCR7, FAIM3, BLK, TNFRSF25, OGT, APBA2, CASK, IL7R, ITGA6 or ARHGEF10, or any combination thereof, compared to the control is detected.

4. The method of claim 1, wherein detecting expression of SNCA and IFI27 comprises detecting mRNA expression of SNCA and IFI27.

5. The method of claim 1, wherein detecting expression of SNCA and IFI27 comprises detecting protein encoded by SNCA and IFI27.

6. The method of claim 1, wherein the sample is a blood sample.

7. The method of claim 1, wherein the subject has prostate cancer and has undergone or is currently undergoing treatment with radiation therapy.

8. The method of claim 1, wherein the appropriate therapy is an agent that decreases expression or activity of SNCA, an agent that decreases expression or activity of IFI27, a psychostimulant drug, a treatment for anemia, cognitive behavior therapy, exercise, or any combination thereof.

9. A method of diagnosing and treating a subject with cancer-related fatigue (CRF), comprising:
   detecting expression of at least one gene associated with CRF in a sample obtained from the subject, wherein the at least one gene is selected from SNCA, SLC25A37 and BCL2L1;
   comparing expression of the at least one gene in the subject to a control;
   diagnosing the subject with CRF if an increase in expression of SNCA, SLC25A37 and BCL2L1 relative to the control is detected; and
   selecting an appropriate therapy for the subject diagnosed with CRF.

10. A method of diagnosing a subject with cancer-related fatigue (CRF), comprising:
    detecting expression of at least one gene associated with CRF in a sample obtained from the subject, wherein the at least one gene is selected from SNCA, SLC25A37 and BCL2L1;
    comparing expression of at least one gene in the subject to a control;
    diagnosing the subject with CRF if an increase in expression of SNCA, SLC25A37 or BCL2L1 relative to the control is detected; and
    providing an appropriate therapy for the subject diagnosed with CRF.

11. The method of claim 10, wherein the appropriate therapy is an agent that decreases expression or activity of SNCA, an agent that decreases expression or activity of SLC25A37, an agent that decreases expression or activity of BCL2L1, a psychostimulant drug, a treatment for anemia, cognitive behavior therapy, exercise, or any combination thereof.

12. The method of claim 10, wherein expression of SNCA, SLC25A37 or BCL2L1 is increased at least 2-fold, at least 3-fold, at least 4-fold or at least 5-fold relative to the control.

13. The method of claim 10, wherein the at least one gene associated with CRF further comprises one or more genes selected from IFI27, CA1, HBD, XK, HBG2, RHCE/RHD, AHSP, GYPB, ISCA1, MS4A1, IGHM, PAX5, FCRLA, TTC3, NSUN5C, POU2AF1, CCR7, FAIM3, BLK, SLC6AS, OR2W3, MYL4, TNFRSF25, OGT, APBA2, CASK, IL7R, ITGA6 and ARHGEF10, and wherein an increase in expression of IFI27, CA1, HBD, XK, HBG2, RHCE/RHD, AHSP, GYPB, ISCA1, SLC6AS, OR2W3 or MYL4, or a decrease in expression of MS4A1, IGHM, PAX5, FCRLA, TTC3, NSUN5C, POU2AF1, CCR7, FAIM3, BLK, TNFRSF25, OGT, APBA2, CASK, IL7R, ITGA6 or ARHGEF10, or any combination thereof, compared to a control, diagnoses the patient with CRF.

14. The method of claim 10, wherein detecting expression of the at least one gene comprises detecting mRNA expression of the at least one gene.

15. The method of claim 10, wherein detecting expression of the at least one gene comprises detecting protein encoded by the at least one gene.

16. The method of claim 10, wherein detecting expression of the at least one gene comprises microarray analysis using a solid support with probes specific for the at least one gene.

17. The method of claim 10, wherein the sample is a blood sample.

* * * * *

UNITED STATES PATENT AND TRADEMARK OFFICE
CERTIFICATE OF CORRECTION

PATENT NO.        : 8,597,883 B2                                    Page 1 of 1
APPLICATION NO.   : 13/396465
DATED             : December 3, 2013
INVENTOR(S)       : Leorey N. Saligan It is certified that error appears in the above-identified patent and that said Letters Patent is hereby corrected as shown below:

On the Title Page:

Item (57) Abstract, line 11, "is array" should read --is an array--

In the Claims:

Column 64, line 38, "comprising detection" should read --comprising detecting--

Column 64, line 39, "more genes" should read --more of genes--

Column 66, line 14, "SLC6AS" should read --SLC6A8--

Column 66, line 17, "SLC6AS" should read --SLC6A8--

Signed and Sealed this
Twenty-ninth Day of September, 2015

Michelle K. Lee
*Director of the United States Patent and Trademark Office*